(12) United States Patent
Cho et al.

(10) Patent No.: US 10,383,602 B2
(45) Date of Patent: Aug. 20, 2019

(54) APPARATUS AND METHOD FOR VISUALIZING ANATOMICAL ELEMENTS IN A MEDICAL IMAGE

(71) Applicant: Samsung Electronics Co., Ltd., Suwon-si (KR)

(72) Inventors: Baek Hwan Cho, Seoul (KR); Yeong Kyeong Seong, Yongin-si (KR); Ye Hoon Kim, Seoul (KR); Ha Young Kim, Yongin-si (KR); Joo Hyuk Jeon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 253 days.

(21) Appl. No.: 14/660,533

(22) Filed: Mar. 17, 2015

(65) Prior Publication Data

US 2015/0265251 A1 Sep. 24, 2015

(30) Foreign Application Priority Data

Mar. 18, 2014 (KR) ........................ 10-2014-0031837

(51) Int. Cl.
*G06K 9/00* (2006.01)
*A61B 8/08* (2006.01)
*G06T 7/00* (2017.01)
*G06T 7/11* (2017.01)
*G06T 7/143* (2017.01)

(52) U.S. Cl.
CPC ............ *A61B 8/5215* (2013.01); *A61B 8/085* (2013.01); *A61B 8/0825* (2013.01); *A61B 8/483* (2013.01);
(Continued)

(58) Field of Classification Search
None
See application file for complete search history.

(56) References Cited

U.S. PATENT DOCUMENTS 5,204,625 A 4/1993 Cline et al.
5,412,563 A 5/1995 Cline et al.
(Continued)

FOREIGN PATENT DOCUMENTS

CN 102369529 A 3/2012
CN 103337074 A 10/2013
(Continued)

OTHER PUBLICATIONS

Ozkan, M., Dawant, B. M., & Maciunas, R. J. (1993). Neural-network-based segmentation of multi-modal medical images: a comparative and prospective study. IEEE transactions on Medical Imaging, 12(3), 534-544.*
(Continued)

*Primary Examiner* — Samah A Beg
(74) *Attorney, Agent, or Firm* — Jefferson IP Law, LLP

(57) ABSTRACT

A method of visualizing anatomical elements in a medical includes receiving a medical image; detecting a plurality of anatomical elements from the medical image; verifying a location of each of the plurality of anatomical elements based on anatomical context information including location relationships between the plurality of anatomical elements; adjusting the location relationships between the plurality of anatomical elements; and combining the verified and adjusted information of the plurality of anatomical elements with the medical image.

30 Claims, 20 Drawing Sheets

(52) U.S. Cl.
CPC .......... *A61B 8/5292* (2013.01); *G06T 7/0012* (2013.01); *G06T 7/11* (2017.01); *G06T 7/143* (2017.01); *G06T 2207/10132* (2013.01); *G06T 2207/20092* (2013.01); *G06T 2207/20128* (2013.01); *G06T 2207/30068* (2013.01)

(56) References Cited

U.S. PATENT DOCUMENTS

| | | | |
|---|---|---|---|
| 6,048,314 A | 4/2000 | Nikom | |
| 6,174,285 B1 | 1/2001 | Clark | |
| 6,264,609 B1 | 7/2001 | Herrington et al. | |
| 6,405,072 B1 | 6/2002 | Cosman | |
| 6,549,646 B1* | 4/2003 | Yeh | G06K 9/6814 382/132 |
| 6,721,447 B1* | 4/2004 | Kim | G06K 9/4652 382/162 |
| 7,092,749 B2 | 8/2006 | Fowkes et al. | |
| 7,615,008 B2 | 11/2009 | Zhang et al. | |
| 7,640,051 B2 | 12/2009 | Krishnan et al. | |
| 7,648,460 B2 | 1/2010 | Simopoulos et al. | |
| 7,678,052 B2 | 3/2010 | Torp et al. | |
| 7,798,965 B2 | 9/2010 | Torp et al. | |
| 7,828,732 B2 | 11/2010 | Wang et al. | |
| 7,953,262 B2 | 5/2011 | Suryanarayanan et al. | |
| 7,995,820 B2 | 8/2011 | de Barros Carneiro et al. | |
| 8,051,386 B2 | 11/2011 | Rosander et al. | |
| 8,064,677 B2 | 11/2011 | Nie et al. | |
| 8,139,832 B2 | 3/2012 | Kshirsagar | |
| 8,150,497 B2 | 4/2012 | Gielen et al. | |
| 8,150,498 B2 | 4/2012 | Gielen et al. | |
| 8,160,341 B2 | 4/2012 | Peng et al. | |
| 8,162,833 B2 | 4/2012 | Zhang et al. | |
| 8,175,354 B2 | 5/2012 | Liang et al. | |
| 8,192,361 B2 | 6/2012 | Sendai | |
| 8,335,364 B2 | 12/2012 | Osmundson et al. | |
| 8,341,100 B2 | 12/2012 | Miller et al. | |
| 8,460,190 B2 | 6/2013 | Jackson et al. | |
| 8,718,341 B2 | 5/2014 | Buelow et al. | |
| 9,532,762 B2 | 1/2017 | Cho et al. | |
| 2003/0194121 A1 | 10/2003 | Eberhard et al. | |
| 2004/0024292 A1 | 2/2004 | Menhardt et al. | |
| 2005/0111715 A1* | 5/2005 | Yoo | G06T 7/0012 382/128 |
| 2005/0171430 A1 | 8/2005 | Zhang et al. | |
| 2005/0207630 A1 | 9/2005 | Chan et al. | |
| 2005/0226495 A1* | 10/2005 | Li | G06K 9/6284 382/159 |
| 2005/0249391 A1* | 11/2005 | Kimmel | G06T 7/11 382/128 |
| 2006/0008143 A1 | 1/2006 | Truyen et al. | |
| 2006/0074287 A1 | 4/2006 | Neumann et al. | |
| 2006/0120608 A1* | 6/2006 | Luo | A61B 8/0825 382/224 |
| 2006/0228015 A1* | 10/2006 | Brockway | G06T 7/0012 382/132 |
| 2008/0107321 A1 | 5/2008 | Oh | |
| 2008/0130833 A1 | 6/2008 | Wang | |
| 2009/0161937 A1 | 6/2009 | Peng et al. | |
| 2009/0306507 A1 | 12/2009 | Hyun et al. | |
| 2010/0124364 A1* | 5/2010 | Huo | G06T 7/0012 382/128 |
| 2010/0158332 A1* | 6/2010 | Rico | A61B 5/4312 382/128 |
| 2010/0256863 A1* | 10/2010 | Nielsen | G07C 5/085 701/31.4 |
| 2010/0266179 A1 | 10/2010 | Ramsay et al. | |
| 2010/0331699 A1 | 12/2010 | Yu et al. | |
| 2011/0007076 A1* | 1/2011 | Nielsen | G06F 17/30241 345/441 |
| 2011/0026791 A1 | 2/2011 | Collins et al. | |
| 2011/0110576 A1* | 5/2011 | Kreeger | G16H 50/50 382/132 |
| 2011/0137132 A1 | 6/2011 | Gustafson | |
| 2011/0263967 A1* | 10/2011 | Bailey | A61B 17/2256 600/411 |
| 2011/0274338 A1* | 11/2011 | Park | G06K 9/6284 382/133 |
| 2011/0280465 A1* | 11/2011 | Wehnes | G06K 9/6267 382/132 |
| 2012/0014585 A1 | 1/2012 | Morita et al. | |
| 2012/0035463 A1 | 2/2012 | Pekar et al. | |
| 2012/0062732 A1* | 3/2012 | Marman | H04N 7/18 348/142 |
| 2012/0099771 A1* | 4/2012 | Lao | G06T 7/0012 382/131 |
| 2012/0101388 A1 | 4/2012 | Tripathi | |
| 2012/0134552 A1* | 5/2012 | Boettger | G06T 7/12 382/128 |
| 2012/0157842 A1 | 6/2012 | Davis et al. | |
| 2012/0165671 A1 | 6/2012 | Hill et al. | |
| 2012/0296213 A1 | 11/2012 | Mauldin, Jr. et al. | |
| 2013/0030278 A1 | 1/2013 | Seong et al. | |
| 2013/0116535 A1 | 5/2013 | Lee et al. | |
| 2013/0236079 A1* | 9/2013 | Carlsen | G01N 23/046 382/132 |
| 2013/0243298 A1* | 9/2013 | Bredno | G06T 5/50 382/131 |
| 2013/0343626 A1 | 12/2013 | Rico et al. | |
| 2014/0033126 A1* | 1/2014 | Kreeger | G06F 19/321 715/821 |
| 2014/0111508 A1 | 4/2014 | Bystrov et al. | |
| 2014/0184608 A1* | 7/2014 | Robb | A61B 5/055 345/440 |
| 2014/0200452 A1* | 7/2014 | Chang | G06F 3/0482 600/437 |
| 2014/0201215 A1* | 7/2014 | Benner | G06F 17/30595 707/748 |
| 2014/0350404 A1* | 11/2014 | Rajguru | A61B 8/06 600/443 |
| 2015/0133784 A1* | 5/2015 | Kapoor | A61B 8/483 600/438 |
| 2015/0230773 A1* | 8/2015 | Cho | A61B 6/5217 382/128 |
| 2015/0265251 A1 | 9/2015 | Cho et al. | |
| 2015/0317792 A1* | 11/2015 | Wiemker | G06T 11/00 382/131 |
| 2016/0078022 A1* | 3/2016 | Lisuk | G06F 3/04842 706/12 |
| 2016/0231886 A1* | 8/2016 | Jo | G01R 33/5608 |
| 2017/0053090 A1 | 2/2017 | Viswanath et al. | |
| 2018/0005381 A1* | 1/2018 | Patel | G06T 7/0014 |
| 2018/0096191 A1 | 4/2018 | Wan et al. | |
| 2018/0136000 A1* | 5/2018 | Rasmusson, Jr. | G01C 21/3638 |
| 2018/0137394 A1* | 5/2018 | Wenzel | G06T 7/0012 |
| 2018/0203998 A1* | 7/2018 | Maisel | G06F 21/565 |

FOREIGN PATENT DOCUMENTS

| | | |
|---|---|---|
| CN | 103608843 A | 2/2014 |
| JP | 2005-533578 A | 11/2005 |
| JP | 2007-524461 A | 8/2007 |
| JP | 2008-501436 A | 1/2008 |
| JP | 2008-161283 A | 7/2008 |
| JP | 2012-20045 A | 2/2012 |
| JP | 2012-511337 A | 5/2012 |
| JP | 2012-512672 A | 6/2012 |
| KR | 10-2009-0127100 A | 12/2009 |
| KR | 10-2011-0039896 A | 4/2011 |
| KR | 10-2013-0012297 A | 2/2013 |
| KR | 10-1258814 B1 | 4/2013 |
| KR | 10-2013-0049638 A | 5/2013 |

OTHER PUBLICATIONS

Archip, Neculai, et al. "A knowledge-based approach to automatic detection of the spinal cord in CT images." IEEE Transactions on medical imaging 21.12 (2002): 1504-1516. (Year: 2002).*

Rucci, M., and E. Lorello. "Organ Segmentation by Means of Neural Networks." Computer Assisted Radiology/Computergestü,tzte

(56) References Cited

OTHER PUBLICATIONS

Radiologie. Springer, Berlin, Heidelberg, 1993. 341-346. (Year: 1993).*

Park, Hyunjin, Peyton H. Bland, and Charles R. Meyer. "Construction of an abdominal probabilistic atlas and its application in segmentation." IEEE Transactions on medical imaging 22.4 (2003): 483-492. (Year: 2003).*

Archip, Neculai, et al. "Lung metastasis detection and visualization on CT images: a knowledge-based method." The Journal of Visualization and Computer Animation 13.1 (2002): 65-76. (Year: 2002).*

G. Hinton et al., "Reducing the Dimensionality of Data with Neural Networks," *Science*, vol. 313, Jul. 28, 2006, pp. 504-507.

M. Zeiler et al., "Adaptive Deconvolutional Networks for Mid and High Level Feature Learning," *Proceedings of the 2011 IEEE International Conference on Computer Vision (ICCV 2011)*, 2011, pp. 2018-2025, conference held Nov. 6-13, 2011, Barcelona, Spain, paper presented on Nov. 10, 2011.

A. Jamieson et al., "Breast Image Feature Learning with Adaptive Deconvolutional Networks," *Proceedings of the SPIE 8315, Medical Imaging 2012: Computer-Aided Diagnosis*, 831506, pp. 1-13, Feb. 23, 2012, conference held Feb. 4-9, 2012, San Diego, California, paper presented on Feb. 7, 2012.

A. Gubern-Merida, et al., "Multi-class Probabilistic Atlas-Based Segmentation Method in Breast MRI," Lecture Notes in Computer Science, vol. 6669, Jan. 2011, pp. 660-667.

Extended European Search Report dated Aug. 21, 2015, in counterpart European Application No. 15159613.7 (11 pages, in English).

Shen et al.; Active Volume Models with Probabilistic Object Boundary Prediction Module; MICCAI 2008, Part I, LNCS 5241; 331-341; Sep. 6, 2008.

Christopher et al.; 3-D Bayesian Ultrasound Breast Image Segmentation Using the EM/MPM Algorithm; Biomedical Imaging; 2002 IEEE; 2002.

European Search Report dated Jan. 2, 2019, issued in European Patent Application No. 18204409.9.

Chinese Office Action dated Feb. 1, 2019, issued in Chinese Patent Application No. 201510118887.9.

Maleike et al. "Interactive segmentation framework of the medical imaging interaction toolkit." Computer methods and programs in biomedicine 96.1 (2009): 72-83. (Year: 2009).

U.S Final Office Action dated Feb. 27, 2019, issued in U.S. Appl. No. 16/010,949.

* cited by examiner

APPARATUS AND METHOD FOR VISUALIZING ANATOMICAL ELEMENTS IN A MEDICAL IMAGE

CROSS-REFERENCE TO RELATED APPLICATIONS

This application claims the benefit under 35 USC 119(a) of Korean Patent Application No. 10-2014-0031837 filed on Mar. 18, 2014, in the Korean Intellectual Property Office, the entire disclosure of which is incorporated herein by reference for all purposes.

BACKGROUND

1. Field

The following description relates to a technique of visualizing anatomical elements included in a medical image.

2. Description of Related Art

Computer-Aided Detection (CAD) is a technique of automatically detecting a lesion from a medical image using a computer for the purpose of assisting a doctor in making a diagnosis. In particular, mammography and breast ultrasonography are two major fields to which CAD is applied to diagnose a lesion. However, due to low resolution and atypical characteristics of medical images, it is difficult to improve accuracy in CAD. For example, ultrasound images captured by a probe whose location and angle are arbitrarily selected by a user are atypical in that locations and angles of the images are not consistent with each other. If an algorithm of automatically detecting a lesion is applied to the atypical images, not only lesions but also anatomical elements may be detected as actual lesions.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for visualizing anatomical elements in a medical image includes an image receiver configured to receive a medical image; an anatomical element detector configured to detect a plurality of anatomical elements from the medical image; an analyzer configured to verify a location of each of the plurality of anatomical elements based on anatomical context information including location relationships between the plurality of anatomical elements, and adjust the location relationships between the plurality of anatomical elements; and an image combiner configured to combine the verified and adjusted information of the plurality of anatomical elements with the medical image.

The medical image may be a breast ultrasound image of a human breast captured using ultrasonic waves; the anatomical element detector may be further configured to detect, from the breast ultrasound image, any two or more of skin, fat, glandular tissue, muscle, and bone; the anatomical context information may include location relationships between the any two or more of skin, fat, glandular tissue, muscle, and bone; and the analyzer may be further configured to perform the verification and the adjustment based on the anatomical context information including the location relationships between the any two or more of skin, fat, glandular tissue, muscle, and bone.

The anatomical element detector may further include a plurality of individual detectors each configured to detect a respective one of the plurality of anatomical elements from the medical image.

Each of the plurality of individual detectors may be further configured to detect the respective one of the plurality of anatomical elements using any one of a deep learning technique, a sliding window technique, and a superpixel technique.

The anatomical element detector may include a single detector configured to detect the plurality of anatomical elements from the medical image simultaneously.

The single detector may be further configured to detect the plurality of anatomical elements from the medical image simultaneously using any one of a deep learning technique, a sliding window technique, and a superpixel technique.

The single detector may be further configured to detect the plurality of anatomical elements from the medical image simultaneously by extracting a plurality of feature maps from the medical image, allocating the plurality of feature maps to corresponding respective anatomical elements, and labeling a location in the medical image of a feature map allocated to a specific anatomical element as the specific anatomical element.

The analyzer may be further configured to adjust a detection result of the plurality of anatomical elements detected from the medical image by the anatomical element detector using a conditional random field technique or a Markov random field technique.

The anatomical context information may further include information on a probability distribution of a location at which each of the anatomical elements is located in the medical image; and the probability distribution may be acquired from pre-established learning data.

The medical image may be one of a plurality of continuous frames or one of a plurality of three-dimensional (3D) images; and the anatomical context information may further include adjacent image information including location information of anatomical elements detected from an adjacent frame or an adjacent cross-section.

The verified and adjusted information of the plurality of anatomical elements to be combined with the medical image may include area information indicating an area of each of the anatomical elements in the medical image.

The area information may include any one or any combination of a contour of an area of each of the plurality of anatomical elements, text representing a name of each of the plurality of anatomical elements, and a color distinguishing an area of each of the plurality of anatomical elements.

The verified and adjusted information of the plurality anatomical elements to be combined with the medical image may include confidence level information indicating a confidence level that each of the plurality of anatomical elements is actually an anatomical element.

The confidence level information may include any one or any combination of text displayed within an area of each of the plurality of anatomical elements; a color of a contour of an area of each of the plurality of anatomical elements; and a transparency of a contour of an area of each of the plurality of anatomical elements.

The verified and adjusted information of the plurality of anatomical elements to be combined with the medical image may be selected by a user from the information of the plurality of anatomical elements.

The verified and adjusted information of the plurality of anatomical elements to be combined with the medical image may include any one or any combination of area information about an area of each of the plurality of anatomical elements in the medical image; confidence level information indicating a confidence level that each of the plurality of anatomical elements is actually an anatomical element; a color or a transparency of a contour of an area of each of the plurality of anatomical elements; a color or a transparency of text representing a name of each of the plurality of anatomical elements; and a transparency of a color layer distinguishing an area of each of the plurality of anatomical elements.

The apparatus may further include a lesion verifier configured to verify whether a region of interest (ROI) detected from the medical image is a lesion based on a lesion detection probability of an anatomical element in which the ROI is located.

In another general aspect, a method of visualizing anatomical elements in a medical image includes receiving a medical image; detecting a plurality of anatomical elements from the medical image; verifying a location of each of the plurality of anatomical elements based on anatomical context information including location relationships between the plurality of anatomical elements; adjusting the location relationships between the plurality of anatomical elements; and combining the verified and adjusted information of the plurality of anatomical elements with the medical image.

The medical image may be a breast ultrasound image of a human breast captured using ultrasonic waves; the detecting of the plurality of anatomical elements may include detecting, from the breast ultrasound image, any two or more of skin, fat, glandular tissue, muscle, and bone; the anatomical context information may include location relationships between the any two or more of skin, fat, glandular tissue, muscle, and bone; and the verifying and the adjusting may include performing the verifying and the adjusting based on the anatomical context information including the location relationships between the any two or more of skin, fat, glandular tissue, muscle, and bone.

The detecting of the plurality of anatomical elements may include individually detecting respective ones of the plurality of anatomical elements from the medical image.

The individually detecting of the respective ones of the plurality of anatomical elements may include individually detecting the respective ones of the plurality of anatomical elements from the medical image using any one of a deep learning technique, a sliding window technique, and a superpixel technique.

The detecting of the plurality of anatomical elements may include simultaneously detecting the plurality of anatomical elements from the medical image.

The simultaneously detecting of the plurality of anatomical elements may include simultaneously detecting the plurality of anatomical elements using any one of a deep learning technique, a sliding window technique, and a superpixel technique.

The simultaneously detecting of the plurality of anatomical elements may include extracting a plurality of feature maps from the medical image; allocating the plurality of feature maps to corresponding respective anatomical elements; and labeling a location in the medical image of a feature map allocated to a specific anatomical element as the specific anatomical element.

The adjusting may include adjusting a detection result of the plurality of anatomical elements detected from the medical image using a conditional random field technique or a Markov random field technique.

The anatomical context information may include information on a probability distribution of a location at which each of the plurality of anatomical elements is located in the medical image; and the probability distribution may be acquired from pre-established learning data.

The medical image may be one of a plurality of continuous frames or one of a plurality of three-dimensional (3D) images; and the anatomical context information may further include adjacent image information including location information of anatomical elements detected from an adjacent frame or an adjacent cross-section.

The verified and adjusted information of the plurality of anatomical elements to be combined with the medical image may include area information indicating an area of each of the plurality of anatomical elements in the medical image.

The area information may include any one or any combination of a contour of an area of each of the plurality of anatomical elements, text representing a name of each of the plurality of anatomical elements, and a color of an area distinguishing each of the plurality of anatomical elements.

The verified and adjusted information of the plurality of anatomical elements to be combined with the medical image may further include confidence level information indicating a confidence level that each of the plurality of anatomical elements is actually an anatomical element.

The confidence level information may include any one or any combination of text within an area of each of the plurality of anatomical elements, a color of a contour of an area of each of the plurality of anatomical elements, and a transparency of a contour of an area of each of the plurality of anatomical elements.

The method may further include selecting the verified and adjusted information of the plurality of anatomical elements to be combined with the medical image from the information of the plurality of anatomical elements in accordance with a user's instruction.

The verified and adjusted information of the anatomical elements to be combined with the medical image may include any one or any combination of area information about an area of each of the plurality of anatomical elements in the medical image; confidence level information indicating a confidence level that each of the plurality of anatomical elements is actually an anatomical element; a color or a transparency of an area of each of the plurality of anatomical elements; a color or a transparency of text representing a name of each of the plurality of anatomical elements; and a transparency of a color layer distinguishing an area of each of the plurality of anatomical elements.

The method may further include verifying whether a region of interest (ROI) detected from the medical image is a lesion based on a lesion detection probability of an anatomical element in which the detected ROI is located.

In another general aspect, a method of visualizing anatomical elements in a medical image includes detecting a plurality of anatomical elements from a medical image; correcting boundaries of the detected anatomical elements to match actual boundaries of the anatomical elements in the medical image based on anatomical context information including location relationships between the plurality of anatomical elements; and combining anatomical element information of the detected anatomical elements having the corrected boundaries with the medical image.

The method may further include ignoring any detected anatomical element that does not correspond to an actual anatomical element in the medical image based on the anatomical context information.

The method may further include selecting the anatomical element information to be combined with the medical image in accordance with a user's instruction.

Other features and aspects will be apparent from the following detailed description, the drawings, and the claims.

DETAILED DESCRIPTION

Figure 1:
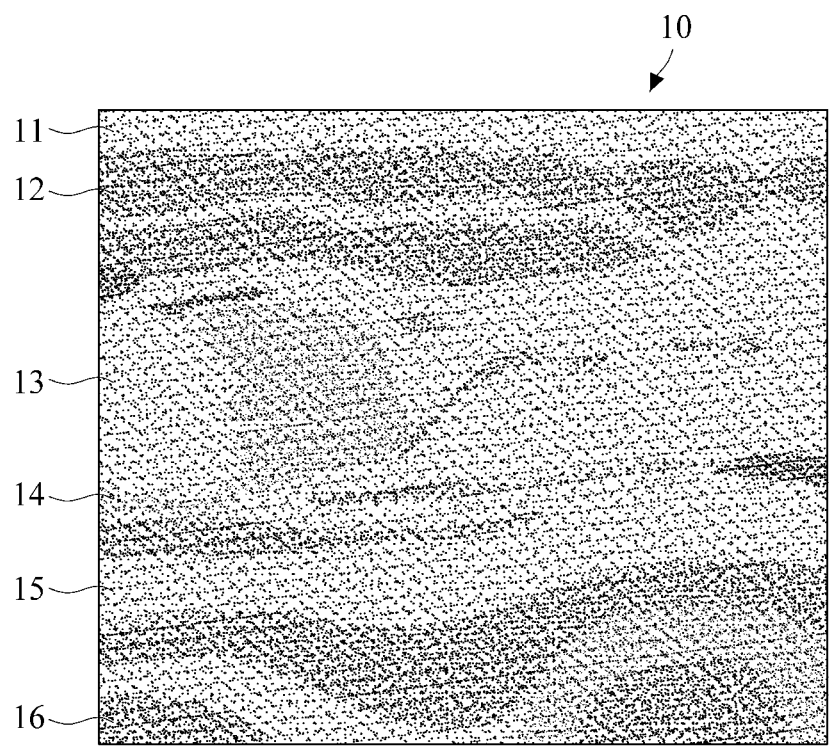
FIG. 1 illustrates an example of an anatomical structure in a breast ultrasound image.

The following description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

This application describes a technology that may be implemented as part of Computer-Aided diagnosis (CAD) in an apparatus and a method for visualizing anatomical elements in a medical image. For example, the technology may be used for visualization of a breast medical images that are generated by a mammogram or a breast ultrasonogram.

In the following description, the term "anatomical element" denotes an element that is distinguished by a particular anatomical property or function. For example, anatomical elements of a breast include skin, subcutaneous fat, glandular tissue, retromammary fat, a pectoralis muscle, and a rib.

In addition, the term "anatomical structure" denotes a structure in which anatomical elements are combined or arranged in a particular relationship with one another. For example, an anatomical structure that can be seen in a breast ultrasound image is a structure in which a breast includes skin located on top, and subcutaneous fat, glandular tissue, retromammary fat, a pectoralis muscle, and a rib located below the skin in the order listed.

An apparatus and a method for visualizing anatomical elements in a medical image is a technology of identifying and visualizing anatomical elements in a medical image. In the apparatus and the method, anatomical elements are first detected from an image. Then, locations of the detected anatomical elements and location relationships between the detected anatomical elements are analyzed, i.e., verified and adjusted, based on anatomical context information. Finally, the verified and adjusted anatomical element information is combined with the original image.

In one example, a medical image may be a breast ultrasound image of a human breast captured using ultrasonic waves. Anatomical elements, such as skin, fat, glandular tissue, muscle, and bone are detected from the breast ultrasound image.

In one example, anatomical elements may be detected individually from one breast ultrasound image. In this case, various deep learning techniques known to one of ordinary skill in the art, such as a convolutional neural network, a convolutional deep belief network, deconvolutional deep learning, or any other deep learning technique known to one of ordinary skill in the art, may be used. In this example, a different detector may be used for each anatomical element, for example, a skin detector for detecting skin, a fat detector for detecting fat, a glandular tissue detector for detecting glandular tissue, a muscle detector for detecting muscle, and a bone detector for detecting bone.

In another example, anatomical elements may be detected simultaneously from a breast ultrasound image. In this case, a sliding window technique or a superpixel technique may be used. In this example, various feature maps may be first extracted from a breast ultrasound image, the extracted feature maps may be allocated to corresponding anatomical elements, and then locations of feature maps allocated to specific anatomical elements may be labeled with the names of the specific anatomical elements.

Anatomical elements detected in this manner, such as skin, fat, muscle, and bone, may be analyzed, i.e., verified and adjusted, based on anatomical context information indicating location relationships between the anatomical elements.

The anatomical context information may include domain knowledge including, for example, "a specific part of a human body has anatomical elements with a predefined anatomical structure thereof" and "identical anatomical elements are gathered", or the like. The expression "identical anatomical elements are gathered" refers to a structure in which a plurality of the same anatomical element are grouped together, for example, a plurality of "muscle" anatomical elements in a muscle layer, or a plurality of "bone" anatomical elements in a bone layer. In addition, the anatomical context information may include a probability distribution of a location at which each anatomical element is located in a medical image of a specific body part. The probability distribution may be acquired based on pre-established training data. Further, if a medical image is one of a plurality of continuous two-dimensional (2D) frames or one of a plurality of three-dimensional (3D) images, the anatomical context information may include location information of an anatomical element acquired from an adjacent frame or an adjacent cross-section.

The verified and adjusted anatomical element information to be combined with the original image may include an area and/or a confidence level of each anatomical element. An area of an anatomical element indicates an area occupied by the anatomical element in the original image. A confidence level of an anatomical element indicates a confidence level as to whether a detected anatomical element is actually an anatomical element. The area and the confidence level of the anatomical element may be displayed using any one or any combination of a contour, text, and a transparency of a color.

In addition, verified and adjusted anatomical element to be combined with the original image may be selected by a user. The user may select for display anatomical element information of all of the anatomical elements in the original image, or may select for display anatomical element information of only some of the anatomical elements in the original image. The user may select for display either one or both of area information and a confidence level of every anatomical element in the original image. The user may select for display information on all or some of anatomical elements in the original image by using any one or more of contours, half-transparent color layers, and text.

Hereinafter, the apparatus and the method for visualizing anatomical elements in a medical image are described with reference to drawings.

Hereinafter, the apparatus and the method are described by taking an example of a 2D breast ultrasound image, but aspects of the present disclosure are not limited thereto. For example, a medical image may be an ultrasound image, an X-ray image, a 2D image, or a 3D image of a breast or a different body part.

FIG. 1 illustrates an example of an anatomical structure in a breast ultrasound image.

Referring to FIG. 1, a two-dimensional ultrasound image 10 of a human breast includes anatomical elements including skin 11, subcutaneous fat 12, glandular tissue 13, retromammary fat 14, a pectoralis muscle 15, and a rib 16. The anatomical elements form an anatomical structure in which the skin 11, the subcutaneous fat 12, the glandular tissue 13, the retromammary fat 14, the pectoralis muscle 15, and the rib 16 are arranged from the surface to the inside in the order listed. However, if one is not a skilled doctor, it is very difficult to distinguish such an anatomical structure from a breast ultrasound image. An example of an apparatus and a method for visualizing anatomical elements in a medical image can automatically sort identify the anatomical elements from the medical image as shown in FIG. 1 and present the identified anatomical elements in a user-friendly way.

Figure 2:
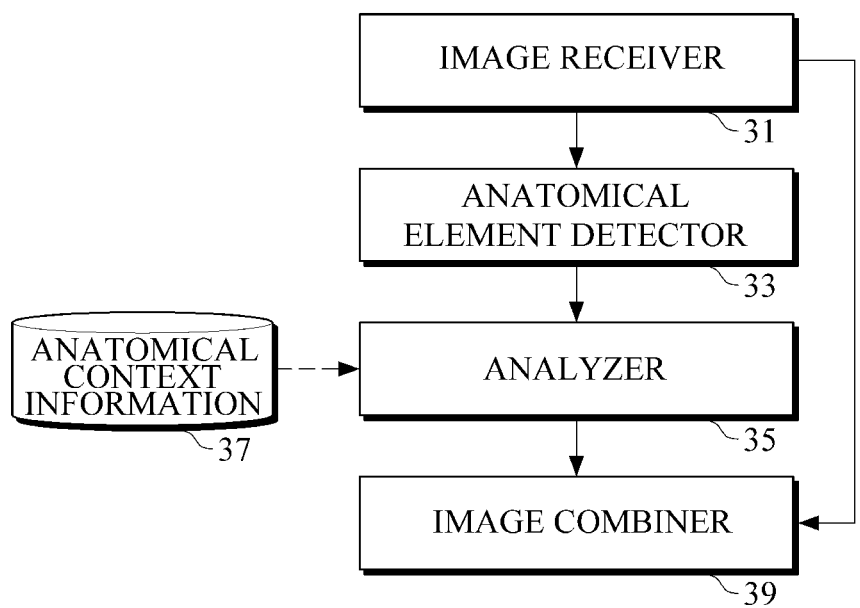
FIG. 2 illustrates an example of an apparatus for visualizing anatomical elements in a medical image.

FIG. 2 illustrates an example of an apparatus for visualizing anatomical elements in a medical image.

Referring to FIG. 2, an apparatus 30 for visualizing anatomical elements includes an image receiver 31, an anatomical element detector 33, an analyzer 35, anatomical context information 37, and an image combiner 39.

The image receiver 31 is a component for receiving a medical image. A medical image may be, for example, an ultrasound image of a human breast that is captured using ultrasonic waves as shown in FIG. 1. The medical image may be received from a medical image diagnostic/capturing device, from an imaging apparatus that captures a specific part of a human body using ultrasonic waves or X-rays, or from a storage device that stores medical images captured by the medical image diagnostic/capturing device or the imaging apparatus.

The anatomical element detector 33 and the analyzer 35 detect anatomical elements by analyzing a medical image to identify the anatomical elements by verifying and adjusting the anatomical elements based on anatomical context information.

The anatomical element detector 33 detects a plurality of anatomical elements from a medical image. If a medical image is the ultrasound breast ultrasound image 10, the anatomical element detector 33 detects skin, fat, glandular tissue, muscle, and bone as anatomical elements from the image 10. Examples of the anatomical element detector 33 are described in detail with reference to FIGS. 4 and 5.

The analyzer 35 verifies and adjusts the anatomical elements detected by the anatomical element detector 33 based on the anatomical context information 37. The anatomical context information 37 includes information indicating location relationships between anatomical elements. If a medical image is the breast ultrasound image 10, the analyzer 35 uses anatomical context information 37 indicating location relationships between anatomical elements such as skin, fat, glandular tissue, muscle, and bone. Based on the anatomical context information indicating the location relationships between the anatomical elements, the analyzer 35 verifies a location of each anatomical element and adjusts location relationships between the anatomical elements throughout the entire area of the medical image.

For example, the anatomical element detector 33 detects the anatomical element "subcutaneous fat" by analyzing the image 10 using a sliding window technique and determining a specific area in the image 10 as "subcutaneous fat with a confidence level of 95%." Similarly, the anatomical element detector 33 detects other anatomical elements, such as "skin", "glandular tissue", "retromammary fat", "a pectoralis muscle", and "a rib."

The analyzer 35 is able to verify whether or not the detected "subcutaneous fat", which looks like subcutaneous fat, is actually subcutaneous fat. For example, based on anatomical context information, for example, information on whether a particular area detected as "subcutaneous fat with a confidence level of 95%" (hereinafter referred to as "area A") is close to other areas detected as "subcutaneous fat with a confidence level of 95%" and information on whether the area A is close to other areas detected as other anatomical elements, such as "skin", "glandular tissue", "retromammary fat", "a pectoralis muscle", and "a rib"

(hereinafter referred to as "area B"), the analyzer is able to verify whether the area A is actually subcutaneous fat.

The analyzer 35 may use a conditional random field (CRF) technique or a Markov random field (MRF) technique, both of which are well known to one of ordinary skill in the art, and thus will not be described in detail here, to adjust the detection result of anatomical elements detected by anatomical element detector 33. For example, if the area A is determined not to be subcutaneous fat, the analyzer 35 adjusts an anatomical element detection result by ignoring the detection result that the area A is "subcutaneous fat with a confidence level of 95%." In another example, assume that the anatomical element detector 33 detects "skin", "subcutaneous fat", "retromammary fat", "a pectoralis muscle", "glandular tissue", and "a rib" in the order listed from top to bottom by analyzing the image 10, thus detecting these anatomical elements in an incorrect order. The analyzer 35 then adjusts the detection result of these anatomical elements based on the anatomical context information to "skin", "subcutaneous fat", "glandular tissue", "retromammary fat", "a pectoralis muscle", and "a rib" in the order listed from top to bottom, thus adjusting location relationships between these anatomical elements so that they are detected in the correct order. Although this example states that the analyzer 35 may use a conditional random field (CRF) technique or a Markov random field (MRF) technique to adjust the detection result of anatomical elements detected by anatomical element detector 33, the analyzer may use other machine learning methods, such as deep learning, that are well known to one of ordinary skill in the art, and thus will not be described in detail here, to adjust the detection result of anatomical elements detected by anatomical element detector 33.

One result of the verifying and adjusting operations is that boundaries of the anatomical elements detected from the image 10 are corrected to match actual boundaries of the anatomical elements in the image 10. Another result of the verifying and adjusting operations is that any detected anatomical elements that do not correspond to actual anatomical elements in the image 10 are ignored.

The image combiner 39 receives the original image 10 from the image receiver 31, and receives an anatomical element detection result analyzed, i.e., verified and adjusted, by the analyzer 35. The image combiner 39 combines the original image 15 with all or part of the verified and adjusted anatomical element detection result by overlaying all or part of the verified and adjusted anatomical element detection result on the original image 15. Examples of a result of the combination are described in detail with reference to FIGS. 7 to 15.

Figure 3:
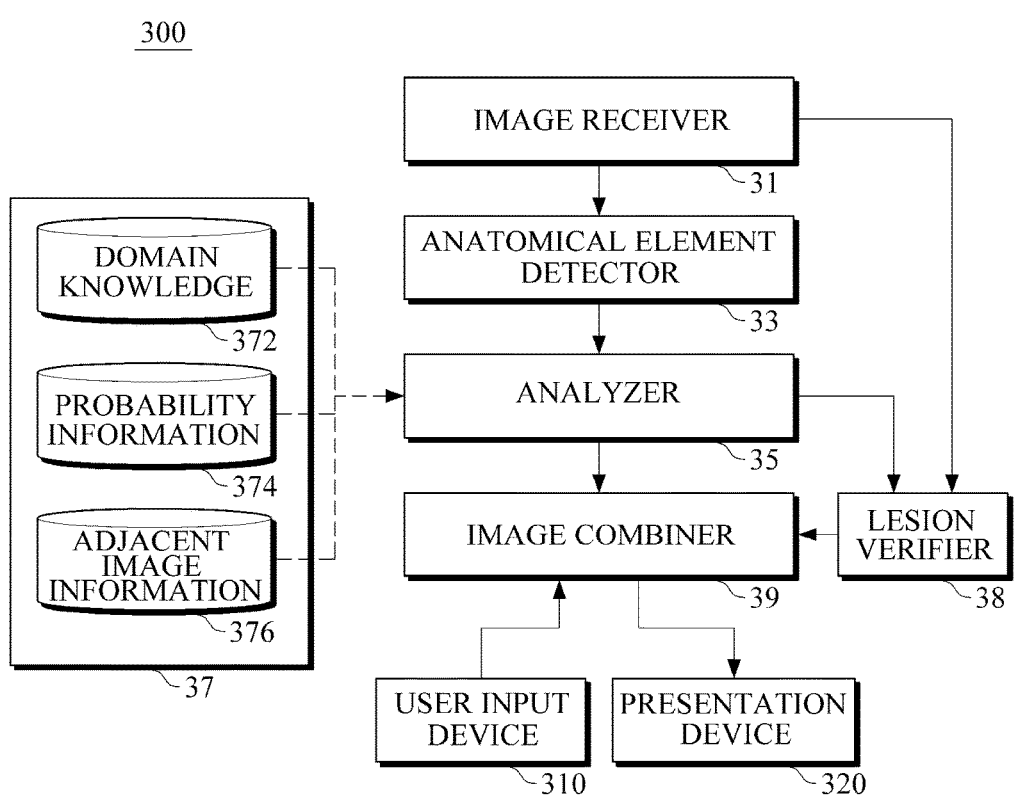
FIG. 3 illustrates another example of an apparatus for visualizing anatomical elements in a medical image.

FIG. 3 illustrates another example of an apparatus for visualizing anatomical elements in a medical image.

Referring to FIG. 3, an apparatus 300 for visualizing anatomical elements includes a user input device 310 and a presentation device 320 in addition to the components 31, 33, 35, 37, and 39 of the apparatus 30 described above with reference to FIG. 2. Moreover, the anatomical context information 37 includes domain knowledge 372, probability information 374, and adjacent image information 376. Further, the apparatus 300 includes include a lesion verifier 38.

The user input device 310 is a device that enables a user to input a command or data to interact with the image combiner 39. The user input device 310 may include any one or any combination of a keyboard, a mouse, a touch-sensitive input device, and a microphone. The presentation device 320 is a device for presenting images combined by the image combiner 39 to the user. The presentation device 320 may include any one or any combination of a display, a printer, a speaker, and a vibration device.

In this example, while displaying a combined image on a display screen, the image combiner 39 provides a user interface that enables a user to input a command. In response to a command from the user input device 310, the image combiner 39 re-combines the image in accordance with the input command and displays the re-combined image on the display screen.

In the anatomical context information 37, the domain knowledge 372 is information indicating location relationships between areas. For example, the domain knowledge 372 includes "a specific part of a human body has predefined anatomical elements", "different anatomical elements have a predefined location relationship in a specific part of a human body", and "identical anatomical elements are gathered." The expression "identical anatomical elements are gathered" refers to a structure in which a plurality of the same anatomical element are grouped together, for example, a plurality of "muscle" anatomical elements in a muscle layer, or a plurality of "bone" anatomical elements in a bone layer. For example, if a medical image is a breast ultrasound image, the domain knowledge 372 may include information indicating, for example, "a breast includes skin, subcutaneous fat, glandular tissue, retromammary fat, a pectoralis muscle, and a rib as anatomical objects."

In the anatomical context information 37, the probability information 374 is acquired from pre-established learning data. The probability information 374 is a probability distribution of a location at which each anatomical element is located in a specific medical image. For example, if a medical image is a breast ultrasound image, the probability information 374 may include information on a probability distribution, such as "skin exists on the top of the image at a probability of 100%", "subcutaneous fat may be found 10 cm away from the top of the image at a probability of 50%", and "a lesion such as a breast cancer cyst may be found between subcutaneous fat and retromammary fat at a probability of 10 to 31%."

In a case where a medical image is one of a plurality of continuous two-dimensional (2D) frames or one of a plurality of three-dimensional (3D) images, the adjacent image information 376 in the anatomical context information 37 includes location information of an anatomical element acquired from an adjacent frame or an adjacent cross-section. For example, if the current medical image is one of a plurality of slices of a 3D ultrasound volume image, previous adjacent slices are analyzed to find out that locations of anatomical elements detected from the previous adjacent slices are highly related to locations of anatomical elements detected from the current medical image. Thus, location information of previously detected anatomical elements included in adjacent image information may be used as useful reference information for verifying and adjusting locations of anatomical elements detected from the current medical image.

The lesion verifier 38 verifies whether a region of interest (ROI) detected from a medical image is a lesion. In one example, the lesion verifier 38 verifies whether an ROI is a lesion with respect to anatomical elements detected from an original image. In practice, chances might be high that a specific lesion is found in one anatomical element, whereas chances might be low that the specific lesion is found in another anatomical element. For example, clinical trials show that a breast cancer lesion is rarely found in fat, but is often found in glandular tissue. The lesion verifier 38 verifies whether or not an ROI is a lesion by determining a type of an anatomical element in which the region of interest (ROI) is located based on the clinical probability data.

In the example of FIG. 3, the lesion verifier 38 receives an original image from the image receiver 31 and detects one or more ROIs from the original image. Then, with reference to anatomical element information determined by the analyzer 35, the lesion verifier 38 determines in which anatomical element each of the detected ROIs is located. Then, the lesion verifier 38 verifies whether or not each ROI is a lesion based on data stored therein that indicates a possibility of a lesion being found in a specific anatomical element. For example, in a case where a medical image is a breast image, if a specific ROI is located in an anatomical element in which breast cancer is rarely found, the lesion verifier 38 determines that the specific ROI is not a lesion. In another example, if a specific ROI is located in an anatomical element in which breast cancer is highly likely to be found, the lesion verifier 38 determines that the specific ROI is likely to be a lesion.

Further, a lesion and/or ROI verified by the lesion verifier 38 is overlaid by the image combiner 39 onto an original image so that the lesion and/or ROI is visually displayed to a user. Thus, for example, on a display screen of a computing device including an apparatus for visualizing anatomical elements in a medical image according to one example, a user can display a specific medical image along with anatomical elements included therein and visualize information on whether a ROI located in an anatomical element in the specific medical image is a lesion.

Figure 4:
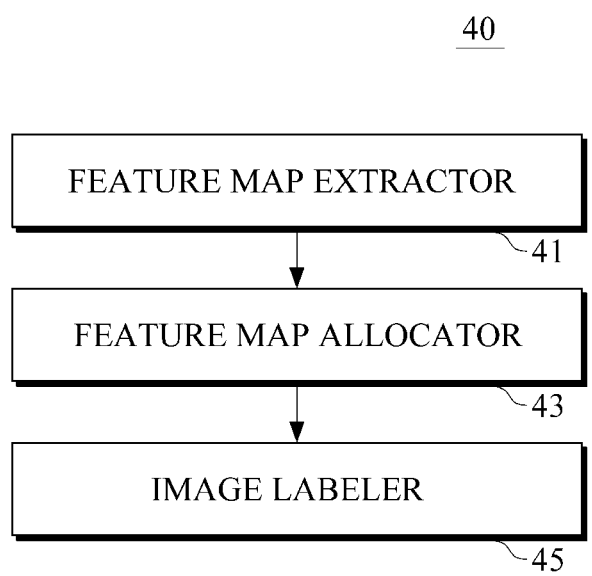
FIG. 4 illustrates an example of an anatomical element detector in FIG. 3.

FIG. 4 illustrates an example of the anatomical element detector 33 in FIG. 3.

Referring to FIG. 4, a single detector 40 that detects all of the anatomical elements from an image simultaneously is an example of the anatomical element detector 33 shown in FIG. 3. In this example, the single detector 40 uses a sliding window technique that uses Histogram of Oriented Gradients (HOG) features. Such a sliding window technique is well known to one of ordinary skill in the art, and thus will not be described in detail here.

The single detector 40 also uses a deep learning technique. Various deep learning techniques are well known to one of ordinary skill in the art, and thus will not be described in detail here. Using feature maps generated through the deep learning technique, the single detector 40 detects anatomical elements. To this end, the single detector 40 includes a feature map extractor 41, a feature map allocator 43, and an image labeler 45. The feature map extractor 41 extracts at least one feature map from an image. The feature map allocator 43 allocates the extracted feature map to a corresponding anatomical element. To this end, the extracted feature map may be compared with a plurality of pre-stored feature maps. If the extracted feature map matches any one of the pre-stored feature maps, the feature map allocator 43 allocates the extracted feature map to an anatomical element that corresponds to the pre-stored feature map matched by the extracted feature map. The image labeler 45 labels a location of a feature map allocated to a specific anatomical element as the specific anatomical element. Accordingly, the location of the feature map allocated to the specific anatomical element is detected as the specific anatomical element. Although in this example, the single detector 40 uses both a sliding window technique and a deep learning technique, in other examples, it may use only the sliding window technique or only the deep learning technique.

In another example, the single detector 40 uses a superpixel technique. In this example, the single detector 40 is configured as a classifier that assigns pixels of an image to superpixels and uses image information such as intensity, texture, and sparse coding features using a deep belief network with respect to each superpixel. Various superpixel techniques are known to one of ordinary skill in the art, and thus will not be described in detail here.

Figure 5:
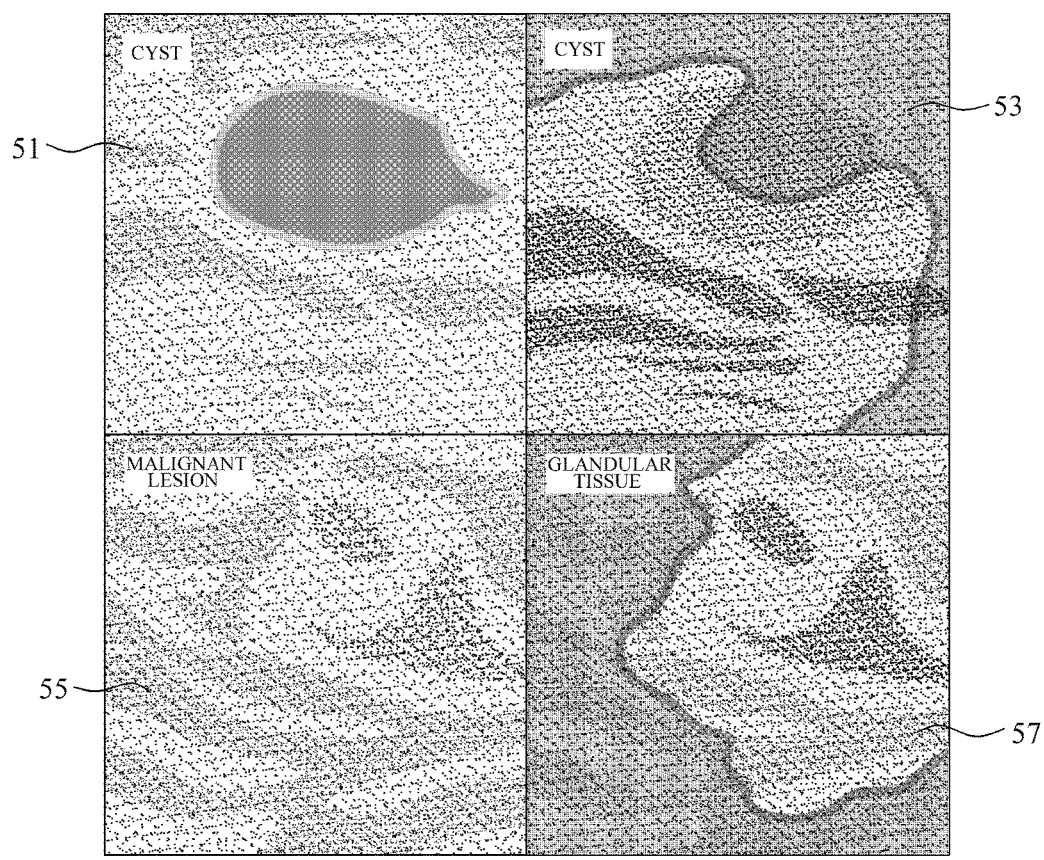
FIG. 5 illustrates examples of feature maps of an anatomical element detector in FIG. 4.

FIG. 5 illustrates examples of feature maps of the anatomical element detector 40 in FIG. 4.

Referring to FIG. 5, a feature map group 50 includes a feature map 51 of a cyst, a feature map 53 of another cyst, a feature map 55 of a malignant lesion, and a feature map 57 of glandular tissue. However, the feature map group 50 is merely an example, and it will be apparent to one of ordinary skill in the art that various other feature maps may be further included to identify more lesions and/or more anatomical structures.

Figure 6:
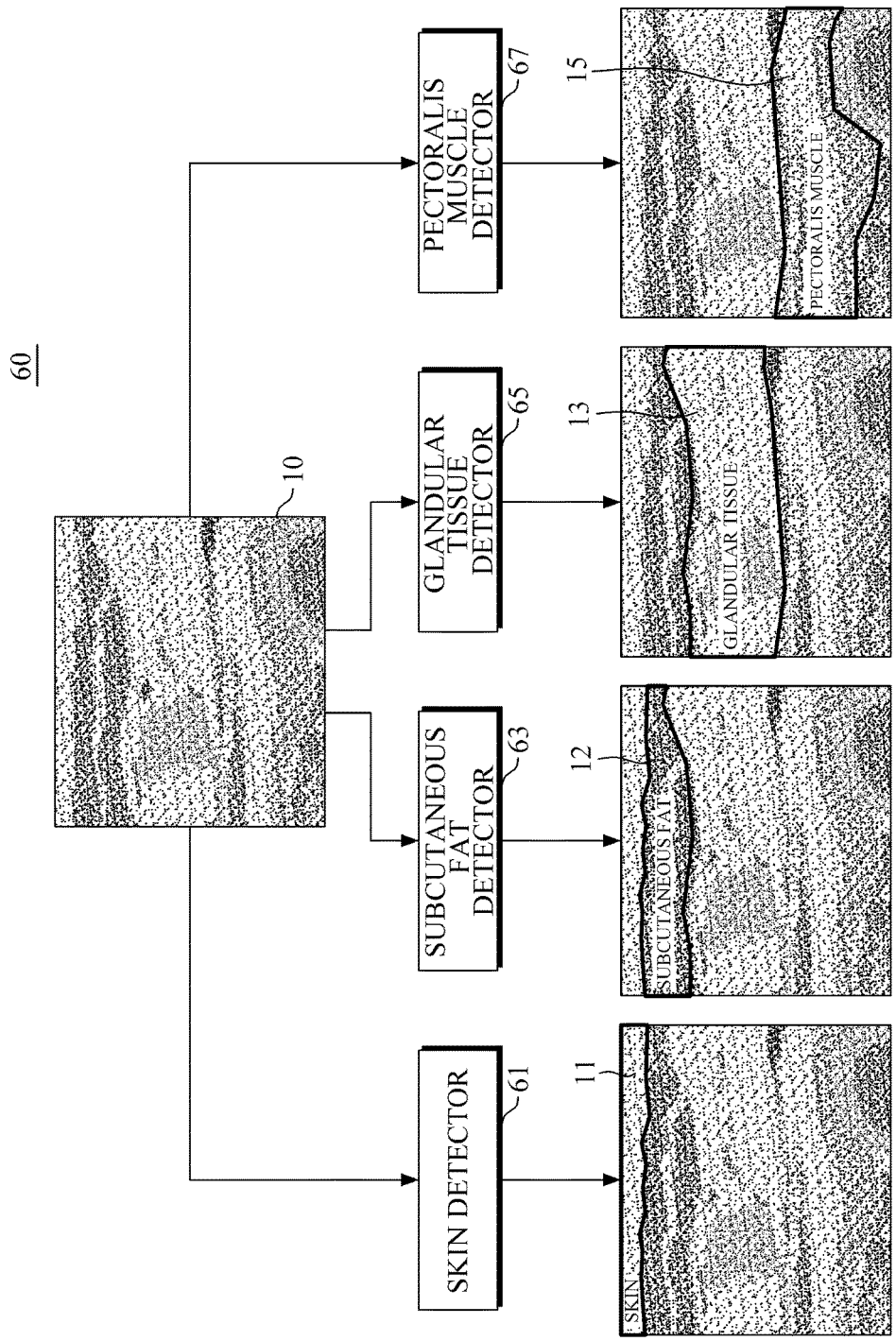
FIG. 6 illustrates another example of the anatomical element detector in FIG. 3.

FIG. 6 illustrates another example of the anatomical element detector 33 in FIG. 3.

Referring to FIG. 6, multiple detectors 60 including a plurality of individual detectors 61, 63, 65, and 67 are an example of the anatomical element detector 33 shown in FIG. 3. The skin detector 61 detects only an area of skin 11 from an original image 10. The subcutaneous fat detector 63 detects only an area of subcutaneous fat 12 from the original image 10. The glandular tissue detector 65 detects only an area of glandular 13 tissue from the original image 10. The pectoralis muscle detector 67 detects only an area of a pectoralis muscle 15 from the original image 10. In this example, each of the individual detectors 61, 63, 65, 67 may use any one of various deep earning techniques known to one of ordinary skill in the art. For example, a convolutional neural network, a deep hierarchical network, a convolutional deep belief network, a deconvolutional deep network, or any other deep learning technique known to one of ordinary skill in the art may be used. Such deep learning techniques are well known to one of ordinary skill in the art, and thus will not be described in detail here. Alternatively, each of the individual detectors 61, 63, 65, 67 may use a sliding window technique or a superpixel technique, both of which are well known to one of ordinary skill in the art, and thus will not be described in detail here.

Figure 7:
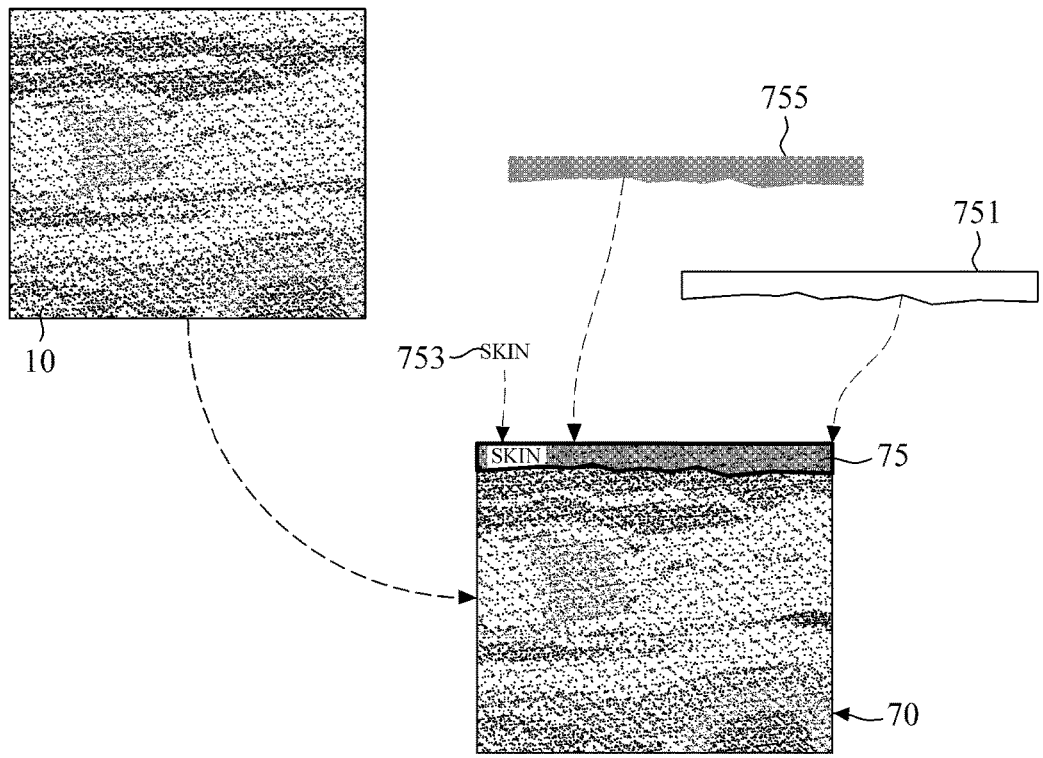
FIG. 7 illustrates an example of a process in which the image combiner in FIG. 3 generates a combined image by overlaying an anatomical structure onto an original image.

FIG. 7 illustrates an example of a process in which the image combiner in FIG. 3 generates a combined image by overlaying an anatomical structure onto an original image.

Referring to FIG. 7, the image combiner 33 generates a combined image 70 by visually overlaying anatomical element information 75 onto the entirety or a part of the original image 10. The anatomical element information 75 may be presented as a color layer 755, a contour 751, text 753, or any combination thereof. The anatomical element information 75 may include a location, a size of an area, and a confidence level of each anatomical element. In addition, the anatomical element information 75 to be combined with the original image 10 may be selected by a user.

FIGS. 8 to 15 illustrate examples of a user interface that provides a menu to enable a user to select specific contents of a combined image generated by an image combiner. However, these examples are merely illustrative, and various other menus with different combinations of options are possible. For example, a user interface may provide a menu that enables a user to select anatomical elements having a confidence level equal to or greater than 50% to be displayed using half-transparent layers.

In addition, FIGS. 8 to 15 illustrate examples of a user interface in which a menu is arranged outside of a window in which an image is being displayed. However, these examples are merely illustrative, and a user interface with a menu having a different arrangement is possible. For example, options of a menu may be selected in response to a user's touch input on a specific location.

Figure 8:
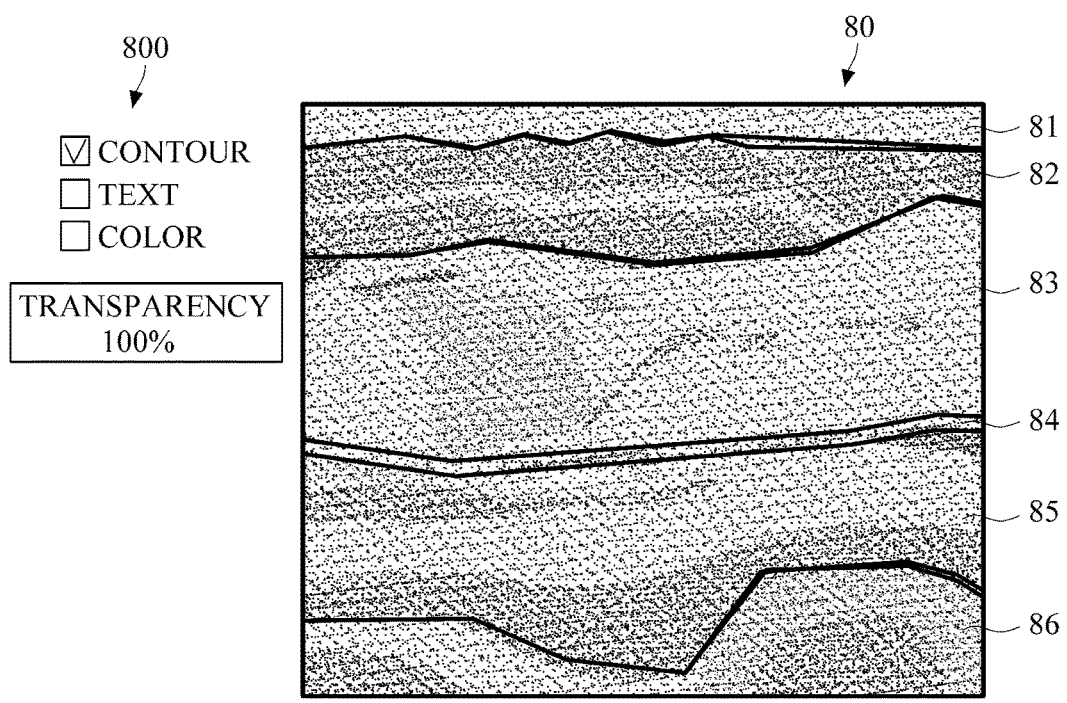
FIG. 8 illustrates an example of a user interface that enables a user to select elements of a combined image generated by the image combiner in FIG. 3.

FIG. 8 illustrates an example of a user interface that enables a user to select elements of a combined image generated by the image combiner 39 in FIG. 3.

Referring to FIG. 8, a user interface provides a user with a menu 800 and a combined image 80. In this example, the menu 800 includes three options. The "contour" option allows a user to select for display areas of anatomical elements using contours. The "text" option allows a user to select for display names of anatomical elements as text. The "color" option allows a user to select for display areas of anatomical elements using a color layer.

In this example, the "transparency" option is provided as a sub-option of the "color" option. The "transparency" option is an option that allows a user to a select a transparency, for example, in a range from 0% to 100%, of a color layer displayed by the "color" option. In this example, only the "color" option has the "transparency" option as a sub-option, but other options may also have the "transparency" option as a sub-option. For example, the "contour" option and the "text" option may also have the "transparency" option as a sub-option to select transparencies of a contour and text. In addition, the "contour" option and the "text" option may further have other sub-options that enable a user to select additional properties of a contour and text, such as a color and a thickness.

In the example of FIG. 8, "contour" is checked in the menu 800, so the combined image 80 is generated by overlaying, onto an original breast ultrasound image, contours delineating skin 81, subcutaneous fat 82, glandular tissue 83, retromammary fat 84, a pectoralis muscle 85, and a rib 86.

Figure 9:
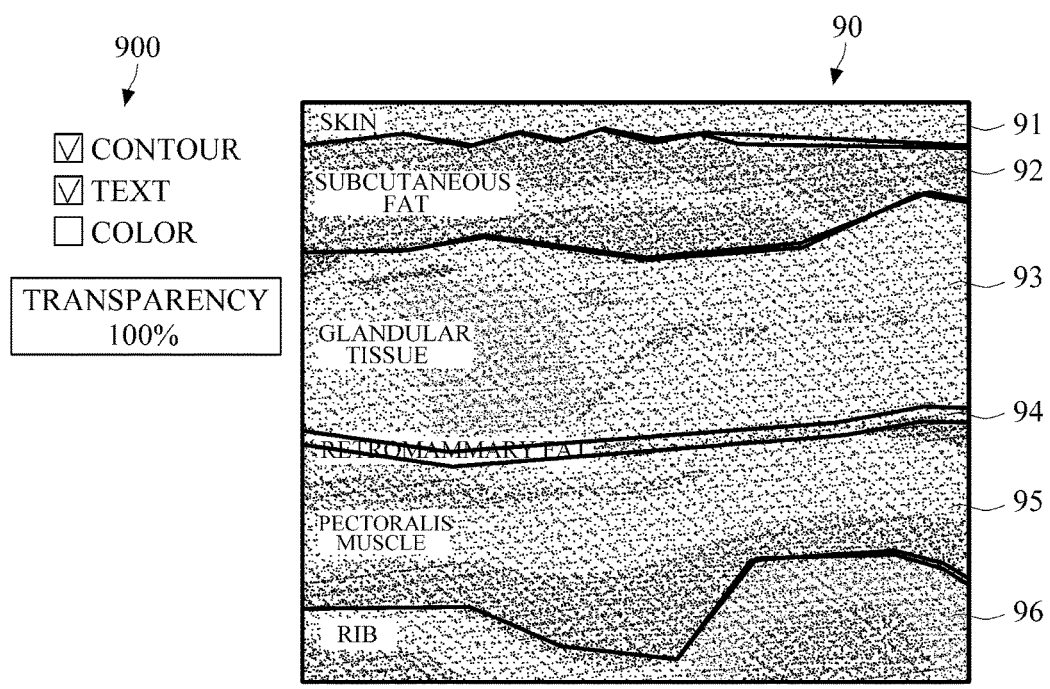
FIG. 9 illustrates another example of a user interface that enables a user to select elements of a combined image generated by the image combiner in FIG. 3.

FIG. 9 illustrates another example of a user interface that enables a user to select elements of a combined image generated by the image combiner 39 in FIG. 3.

Referring to FIG. 9, a user interface provides a user with a menu 900 and a combined image 90. In this example, the menu 900 includes three options and one sub-option, like the menu 800 of FIG. 8.

In the example of FIG. 9, "contour" and "text" are checked in the menu 900, so the combined image 90 is generated by overlaying, onto an original breast ultrasound image, contours delineating skin 91, subcutaneous fat 92, glandular tissue 93, retromammary fat 94, a pectoralis muscle 95, and a rib 96 and text representing the names of these anatomical elements in the corresponding areas.

Figure 10:
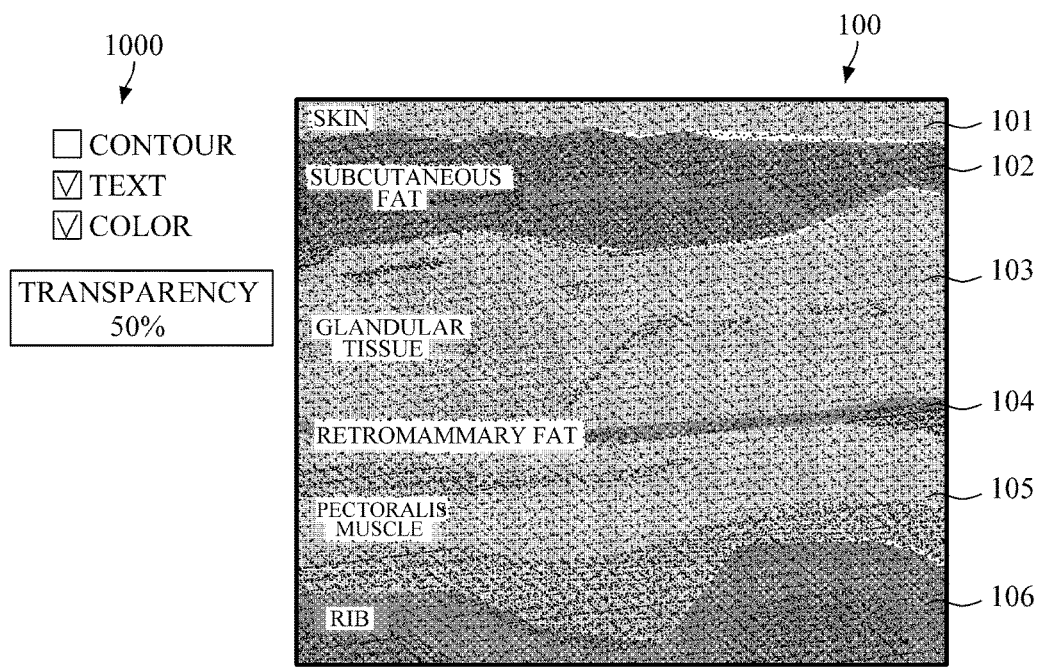
FIG. 10 illustrates another example of a user interface that enables a user to select elements of a combined image is generated by the image combiner in FIG. 3.

FIG. 10 illustrates another example of a user interface that enables a user to select elements of a combined image generated by the image combiner 39 in FIG. 3.

Referring to FIG. 10, a user interface provides a user with a menu 1000 and a combined image 100. In this example, the menu 1000 has three options and one sub-option, like the menu 800 of FIG. 8.

In the example of FIG. 10, "text" and "color" are checked in the selection 1000, and "50%" is set as a transparency for color. Accordingly, the combined image 100 is generated by overlaying, onto an original breast ultrasound image, half-transparent layers of different colors distinguishing skin 101, subcutaneous fat 102, glandular tissue 103, retromammary fat 104, a pectoralis muscle 105, and a rib 106 and text representing the names of these anatomical elements in the corresponding areas.

Figure 11:
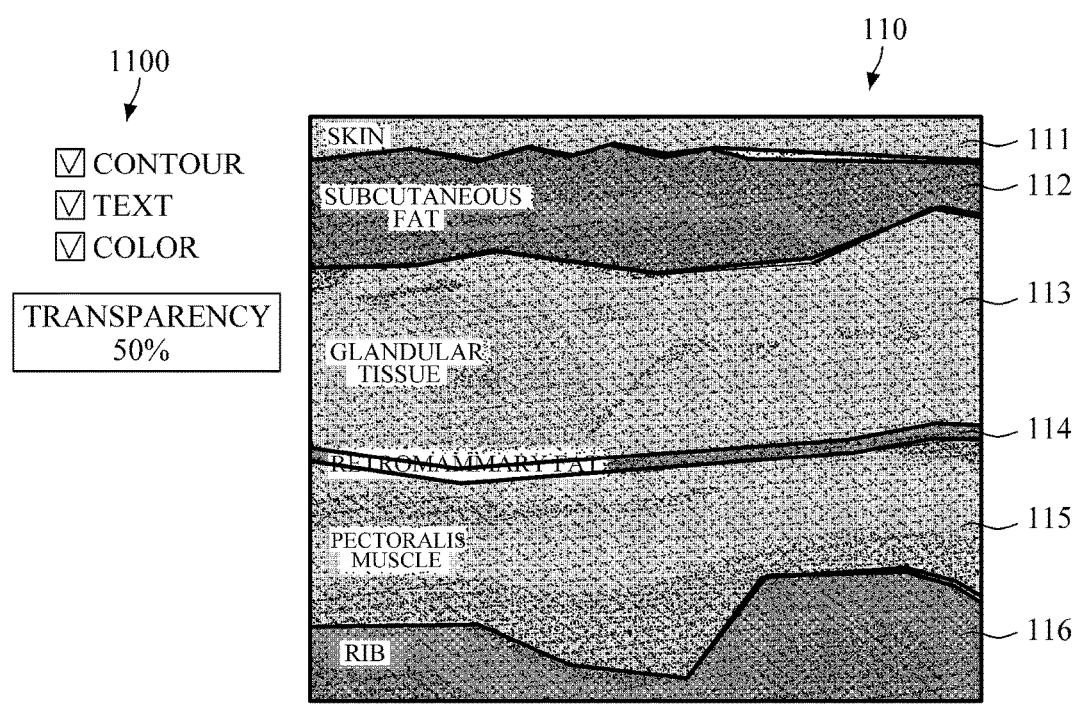
FIG. 11 illustrates another example of a user interface that enables a user to select elements of a combined image is generated by the image combiner in FIG. 3.

FIG. 11 illustrates another example of a user interface that enables a user to select elements of a combined image generated by the image combiner 39 in FIG. 3.

Referring to FIG. 11, a user interface provides a user with a menu 1100 and a combined image 110. In this example, the menu 1100 has three options and one sub-option, like the menu 800 of FIG. 8.

In the example of FIG. 11, "contour", "text", and "color" are checked in the menu 1100, and "50%" is set as a transparency for color. Accordingly, the combined image 110 is generated by overlaying onto an original breast ultrasound image half-transparent layers of different colors distinguishing skin 111, subcutaneous fat 112, glandular tissue 113, retromammary fat 114, a pectoralis muscle 115, and a rib 116, contours delineating these anatomical elements, and text representing the names of these anatomical elements in the corresponding areas.

Figure 12:
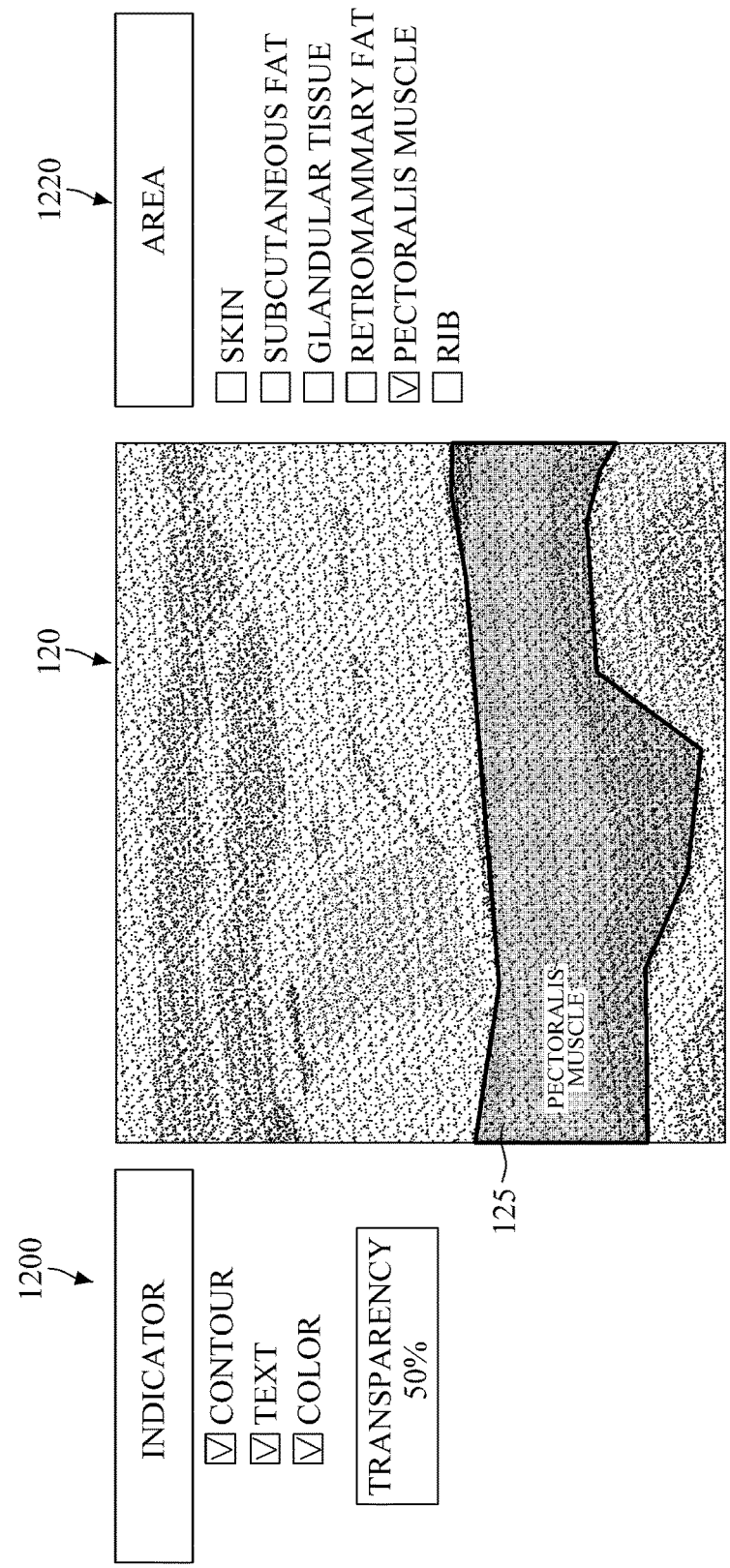
FIG. 12 illustrates another example of a user interface that enables a user to select elements of a combined image is generated by the image combiner in FIG. 3.

FIG. 12 illustrates another example of a user interface that enables a user to select elements of a combined image generated by the image combiner 39 in FIG. 3.

Referring to FIG. 12, a user interface provides a user with two menus 1200 and 1220, and a combined image 120. In this example, the left menu 1200 lists indicators including three options and one sub-option, like the menu 800 shown in FIG. 8. The right menu 1220 lists areas including skin, subcutaneous fat, glandular tissue, retromammary fat, a pectoralis muscle, and a rib.

In the example of FIG. 12, "contour", "text", and "color" are selected in the left menu 1200, "50%" is set as a transparency for color, and "pectoralis muscle" is checked in the right menu 1220. Accordingly, the combined image 120 is generated by overlaying, onto an original breast ultrasound image, a half-transparent layer of one color distinguishing only a pectoralis muscle 125, a contour delineating this anatomical element, and text representing the name of this anatomical element in the corresponding area.

Figure 13:
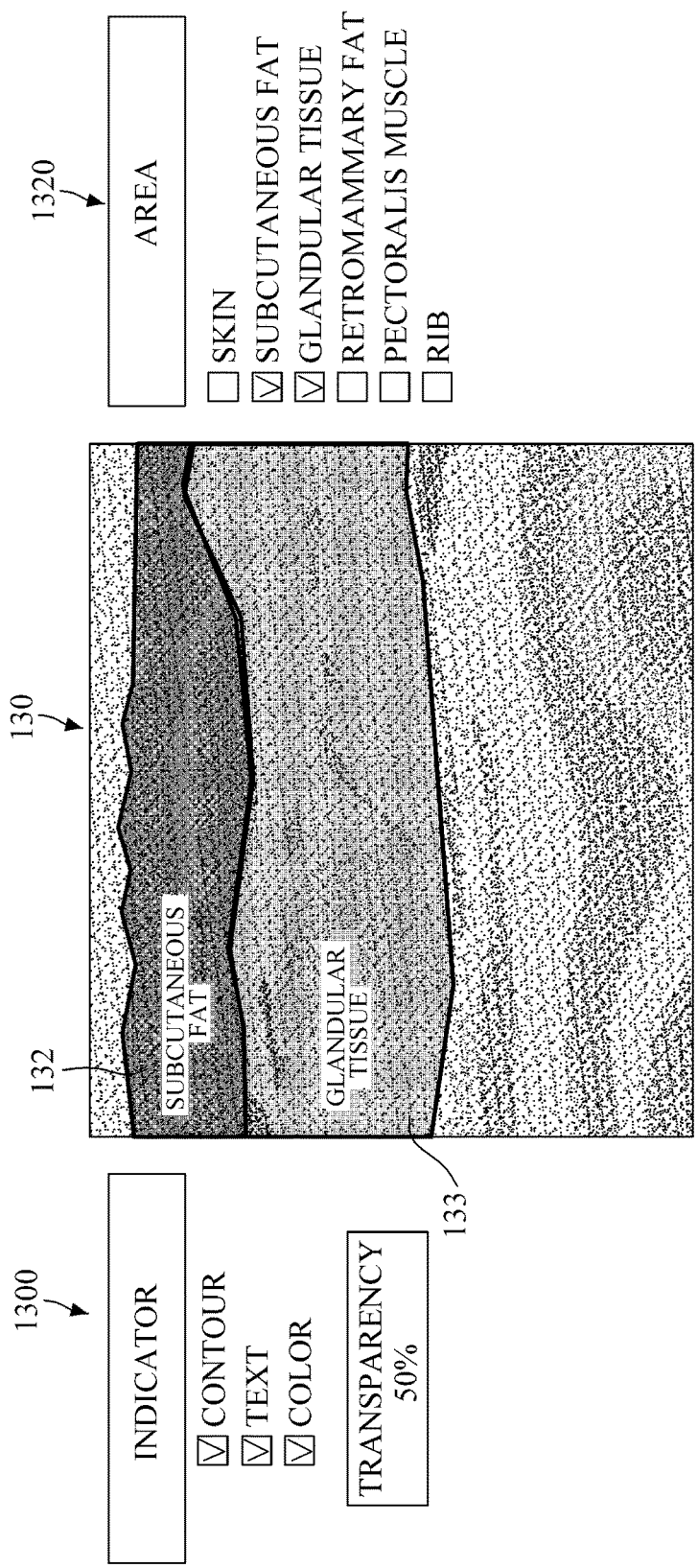
FIG. 13 illustrates another example of a user interface that enables a user to select elements of a combined image is generated by the image combiner in FIG. 3.

FIG. 13 illustrates another example of a user interface that enables a user to select elements of a combined image generated by the image combiner 39 in FIG. 3.

Referring to FIG. 13, a user interface provides a user with two menus 1300 and 1320, and a combined image 130. In this example, the left menu lists indicators including three options and one sub-option, like the menu 800 of FIG. 8. The right menu 1320 lists areas including skin, subcutaneous fat, glandular tissue, retromammary fat, a pectoralis muscle, and a rib.

In the example of FIG. 13, "contour", "text", and "color" are checked in the left menu 1300, "50%" is set as a transparency for color, and "subcutaneous fat" and "glandular tissue" are checked in the right menu 1320. Accordingly, the combined image 130 is generated by overlaying, onto an original breast ultrasound image, half-transparent layers of two different colors distinguishing subcutaneous fat 132 and glandular tissue 133, contours of these anatomical elements, and text representing the names of these anatomical elements in the corresponding areas.

Figure 14:
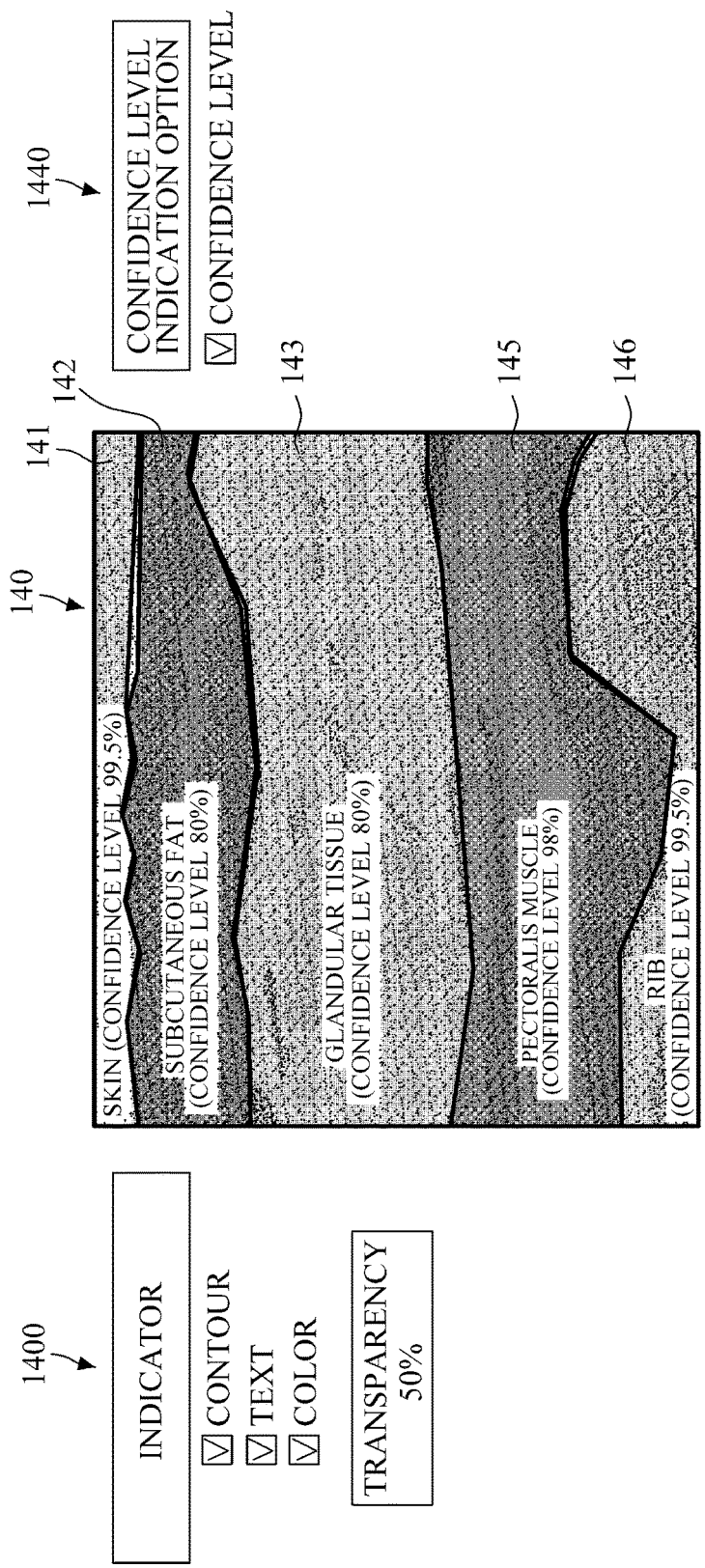
FIG. 14 illustrates another example of a user interface that enables a user to select elements of a combined image is generated by the image combiner in FIG. 3.

FIG. 14 illustrates another example of a user interface that enables a user to select elements of a combined image generated by the image combiner 39 in FIG. 3.

Referring to FIG. 14, a user interface provides a user with two menus 1400 and 1420, and a combined image 140. In this example, the left menu 1400 lists indicators including three options and one sub-option, like the menu 800 of FIG. 8. The right menu 1420 provides a "selection" option that enables displaying a confidence level of each of the anatomical elements. Although only the "selection" option is provided in FIG. 14, additional menu options may be further provided to enable individually displaying a confidence level of each of skin, subcutaneous fat, glandular tissue, retromammary fat, a pectoralis muscle, and a rib, similar to the right menu 1320 of FIG. 13 that enables individual anatomical elements to be displayed.

In the example of FIG. 14, "contour", "text", and "color" are checked in the left menu 1400, "50%" is set as a transparency for color, and "confidence level" is checked in the right menu 1420. Accordingly, the combined image 140 is generated by overlaying, onto an original breast ultrasound image, half-transparent layers of different colors distinguishing each of skin 141, subcutaneous fat 142, glandular tissue 143, a pectoralis muscle 145, and a rib 146, contours delineating these anatomical elements, and text representing the names and the confidence levels of these anatomical elements in the corresponding areas.

In the example of FIG. 14, a confidence level is displayed using a contour, text, and additional text different from a color layer. However, this is not the only way a confidence level may be displayed. A confidence level may be displayed using a contour, text, a color of a color layer, and/or a transparency of a color layer.

Figure 15:
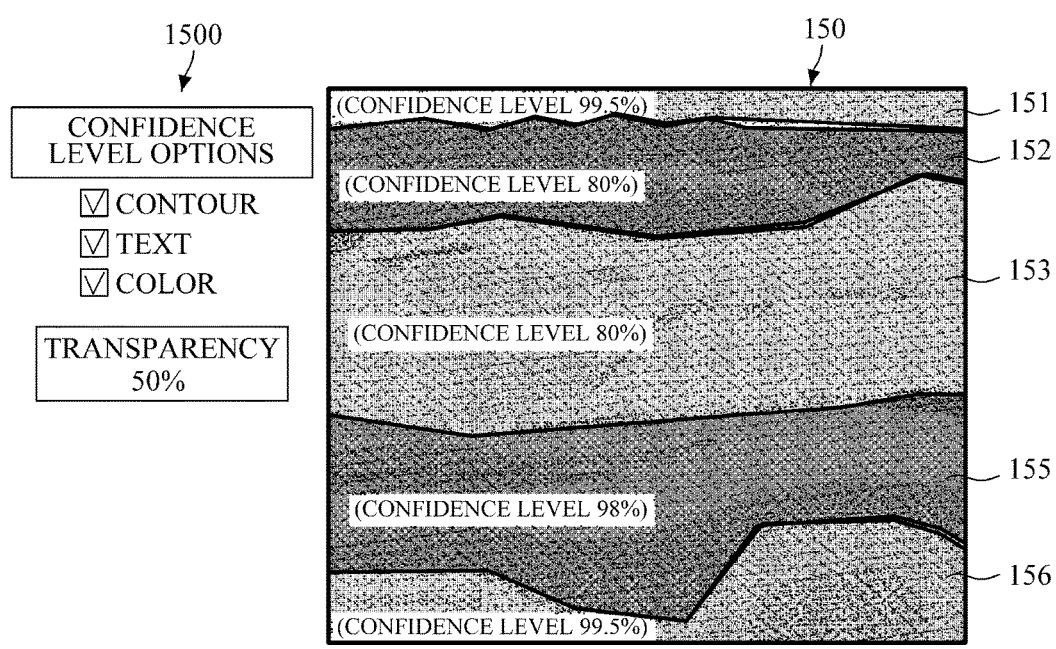
FIG. 15 illustrates another example of a user interface that enables a user to select elements of a combined image is generated by the image combiner in FIG. 3.

FIG. 15 illustrates another example of a user interface that enables a user to select elements of a combined image generated by the image combiner 39 in FIG. 3.

Referring to FIG. 15, a user interface provides a user with a menu 1500 and a combined image 150. In this example, the menu 1500 lists three options. The "contour" option allows a user to select for display an area of each anatomical element using a contour. The "text" option allows a user to select for display a confidence level of each anatomical element, rather than a name thereof, as text. The "color" option allows a user to select for display an area of each anatomical element using a color layer.

In the example of FIG. 15, "contour", "text", and "color" are checked in the menu, and "50%" is set as a transparency for color. Accordingly, the combined image 150 is generated by overlaying, onto an original breast ultrasound image, half-transparent layers of different colors distinguishing skin 151, subcutaneous fat 152, glandular tissue 153, a pectoralis muscle 155, and a rib 156, contours delineating these anatomical elements, and text representing not names but confidence levels of these anatomical elements in the corresponding areas.

Figure 16:
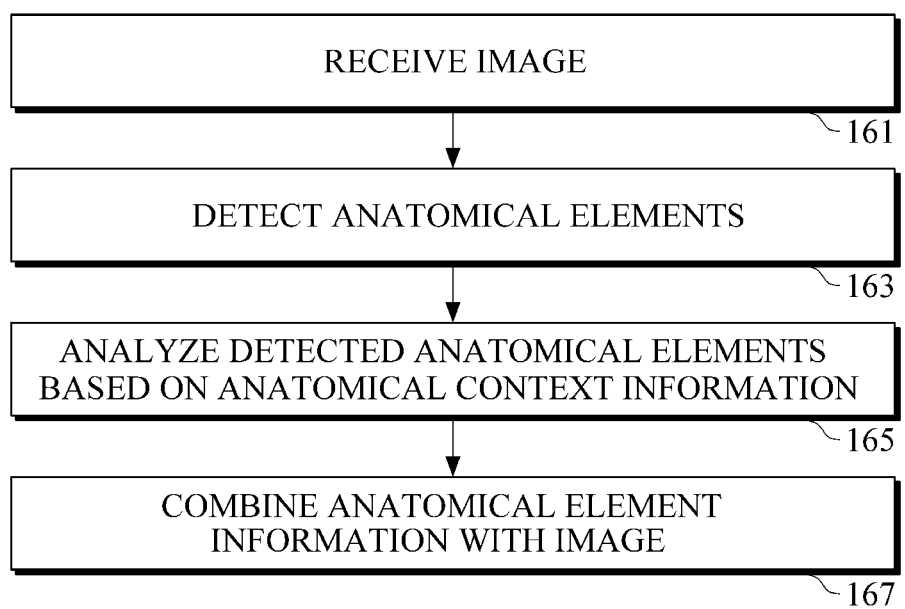
FIG. 16 illustrates an example of a method of visualizing anatomical elements in a medical image.

FIG. 16 illustrates an example of a method of visualizing anatomical elements in a medical image.

Referring to FIG. 16, a method 160 of visualizing anatomical elements includes receiving in 161 a medical image input to the medical image receiver 31 of the apparatus 30 shown in FIG. 2. The medical image may be input from a medical image diagnostic device capturing a specific part of human body, a capturing device, or a storage device storing images captured by such devices.

The received image is analyzed to detect at least one anatomical element existing at a specific location within the image in 163. The detection of anatomical elements may be performed by a plurality of detectors that respectively detect different anatomical elements. Alternatively, the detection of anatomical elements may be performed by a single detector that detects all of the anatomical elements from an image at once. In operation 163, if the received image is a breast ultrasound image, skin, subcutaneous fat, glandular tissue, retromammary fat, a pectoralis muscle, and a rib are detected.

The detected anatomical elements are analyzed in 165 based on anatomical context information including location relationships between the anatomical elements. For example, if a received image is a breast ultrasound image, anatomical context information indicating location relationships between detected anatomical elements of a breast, such as skin, subcutaneous fat, glandular tissue, retromammary fat, a pectoralis muscle, and a rib, may be used.

Lastly, anatomical element information about the analyzed anatomical elements is combined with an original image in 167. For example, a name of each anatomical element, a location and a size of an area of each anatomical element in an original image, and a confidence level of each anatomical element are visually overlaid onto the original image.

Figure 17:
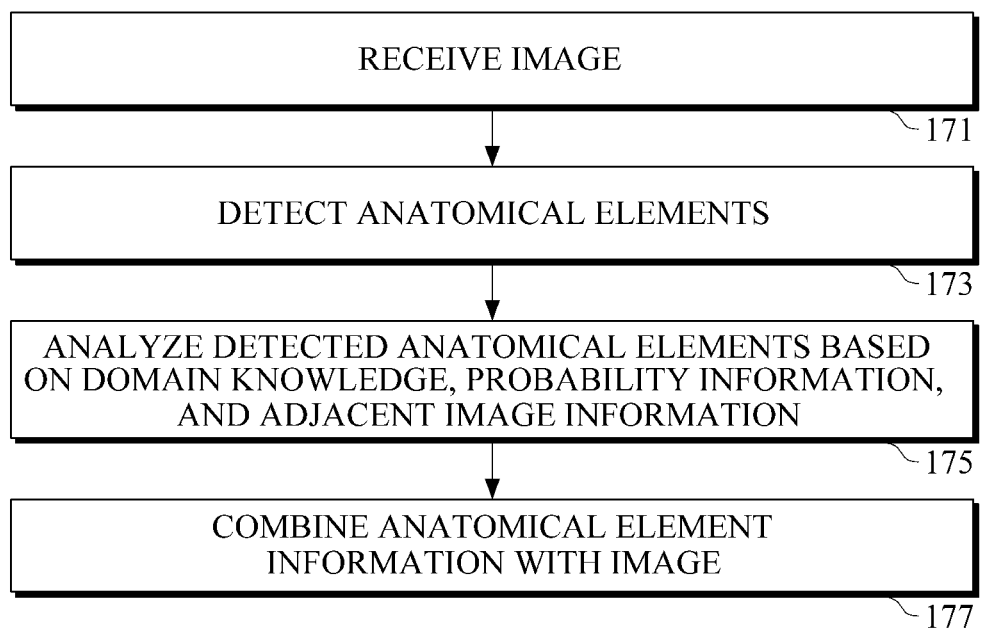
FIG. 17 illustrates another example of a method of visualizing anatomical elements in a medical image.

FIG. 17 illustrates another example of a method of visualizing anatomical elements in a medical image.

Referring to FIG. 17, a method 170 of visualizing anatomical elements in a medical image includes receiving in 171 a medical image input to the medical image receiver 31 of the apparatus 30 shown in FIG. 3. In 173, if the received image is a breast ultrasound image, skin, subcutaneous fat, glandular tissue, retromammary fat, a pectoralis muscle, and a rib are detected as anatomical elements. In 175, the anatomical elements are analyzed based on anatomical context information including domain knowledge indicating location relationships between the anatomical elements, probability information, and adjacent image information.

In the anatomical context information, the domain knowledge indicates location relationships between areas. For example, if the received medical image is a breast ultrasound image, domain knowledge may include information such as "a breast includes skin, subcutaneous fat, glandular tissue, retromammary fat, a pectoralis muscle, and a rib as anatomical objects" and "a breast includes skin located on top, and subcutaneous fat, glandular tissue, retromammary fat, a pectoralis muscle, and a rib located below the skin in the order listed."

The probability information is a probability distribution of a location at which each anatomical element is located in the image. For example, the probability information may include information on a probability distribution, such as "skin exists on the top of the image at a probability of 100%", "subcutaneous fat may be found 10 cm away from the top of the image at a probability of 50%", and "a lesion such as a breast cancer cyst may be found between subcutaneous fat and retromammary fat at a probability of 10 to 31%."

The adjacent image information is information on an image temporally or spatially adjacent to the current medical image. For example, if the current medical image is one of a plurality of 2D continuous frames or one of a plurality of 3D cross-sectional images, locations of anatomical elements detected from a previous medical image may be highly related to locations of anatomical elements detected from the current medical image. Thus, location information of previously detected anatomical elements included in the adjacent image information may be used as useful reference information to verify and adjust locations of anatomical elements detected from the current image.

Lastly, anatomical element information of verified and adjusted anatomical elements is combined with an original image in 177. For example, a name of each anatomical element, a location and a size of an area of each anatomical element in the original image, and a confidence level of each anatomical element are visually overlaid onto the original image.

Figure 18:
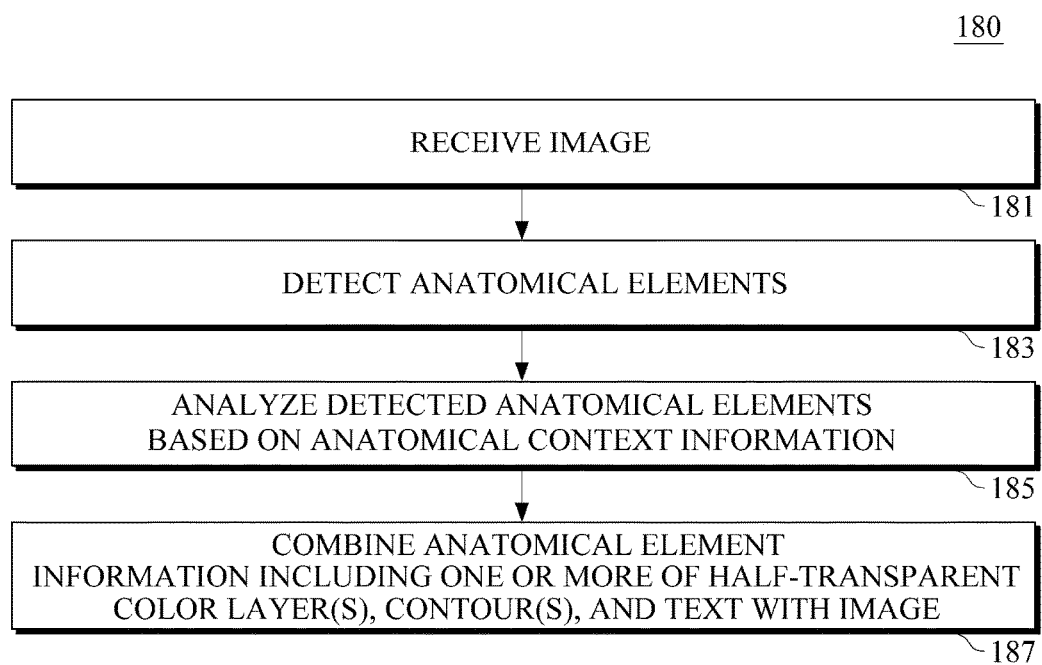
FIG. 18 illustrates another example of a method of visualizing anatomical elements in a medical image.

FIG. 18 illustrates another example of a method of visualizing anatomical elements in a medical image.

Referring to FIG. 18, a method 180 of visualizing anatomical elements in a medical image includes receiving in 181 a medical image input to the medical image receiver 31 of the apparatus 30 shown in FIG. 2 or 3. In 183, if the received image is a breast ultrasound image, skin, subcutaneous fat, glandular tissue, retromammary fat, a pectoralis muscle, and a rib are detected as anatomical elements. In 185, the anatomical elements are analyzed based on anatomical context information including location relationships between the anatomical elements.

In 187, anatomical element information of the analyzed anatomical elements are combined with an original image. For example, any one or more of half-transparent layers of different colors distinguishing each of the anatomical elements, contours delineating each of the anatomical elements, and text representing the names of each of the anatomical elements in the corresponding areas may be visually overlaid onto the original image.

Figure 19:
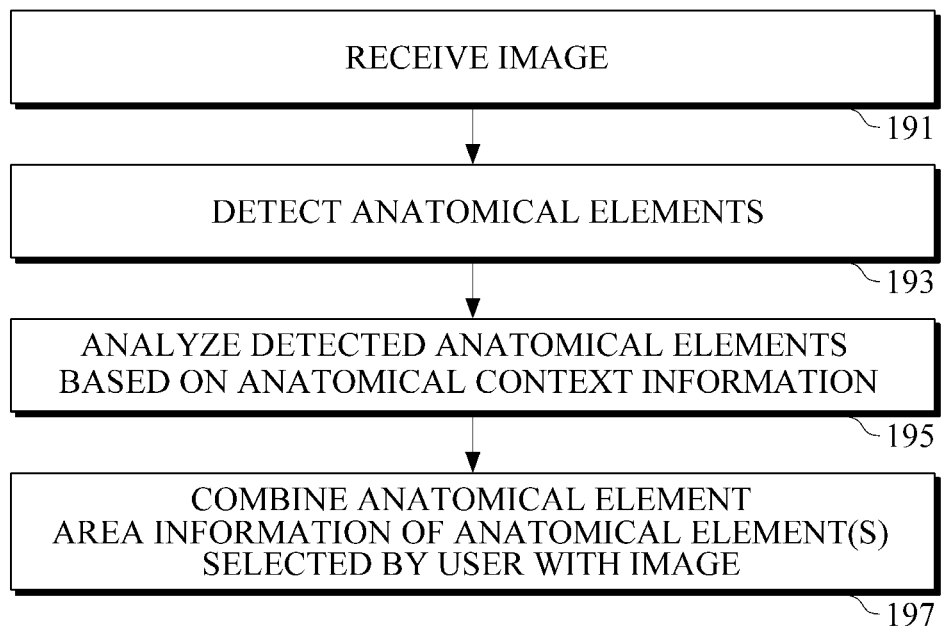
FIG. 19 illustrates another example of a method of visualizing anatomical elements in a medical image.

FIG. 19 illustrates another example of a method of visualizing anatomical elements in a medical image.

Referring to FIG. 19, a method 190 of visualizing anatomical elements in a medical image includes receiving in 191 a medical image input to the medical image receiver 31 of the apparatus 30 shown in FIG. 2 or 3. In 193, if the received medical image is a breast ultrasound image, skin, subcutaneous fat, glandular tissue, retromammary fat, a pectoralis muscle, and a rib are detected as anatomical elements. In 195, the anatomical elements are analyzed based on anatomical context information including location relationships between the anatomical elements.

In 197, among anatomical element information of all of the analyzed anatomical elements, only anatomical element area information of one or more anatomical elements selected by a user is combined with an original image. For example, if skin, subcutaneous fat, glandular tissue, retromammary fat, a pectoralis muscle, and a rib are detected as anatomical elements, the user may select any desired anatomical element therefrom. For example, the user may select only skin, may select both subcutaneous fat and glandular tissue, or may select all of the detected anatomical elements. Then, anatomical element area information of each of the selected anatomical elements are visually overlaid onto the original image. For example, any one or more of half-transparent layers of different colors distinguishing each of the selected anatomical elements, contours delineating each of the selected anatomical elements, and text representing the names of each of the selected anatomical elements in the corresponding areas may be visually overlaid onto the original image.

Figure 20:
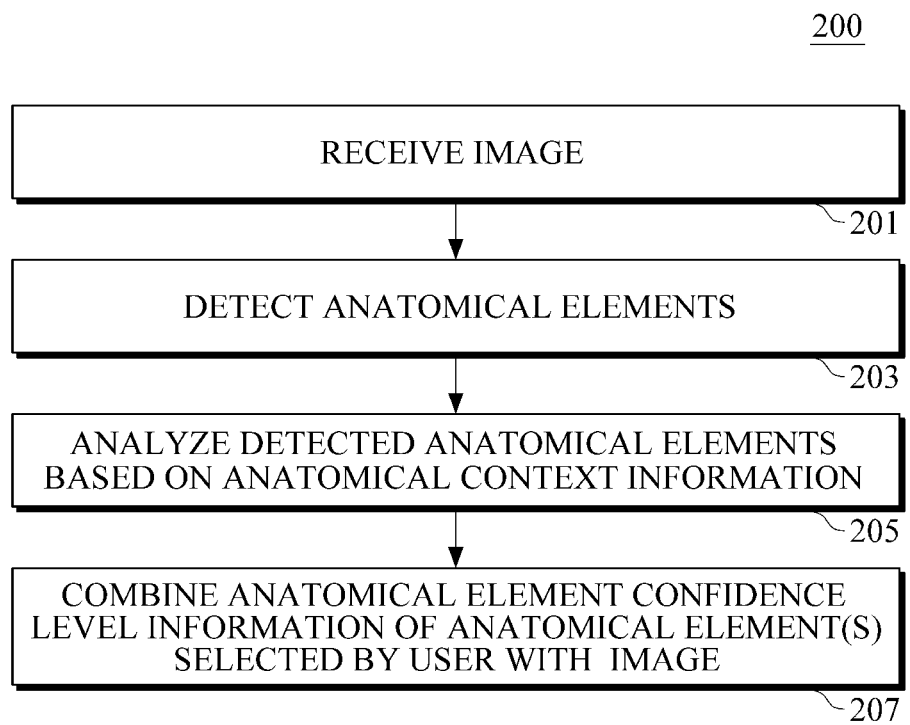
FIG. 20 illustrates another example of a method of visualizing anatomical elements in a medical image.

FIG. 20 illustrates another example of a method of visualizing anatomical elements in a medical image.

Referring to FIG. 20, a method 200 of visualizing anatomical elements in a medical image includes receiving in 201 a medical image input to the medical image receiver 31 of the apparatus 30 shown in FIG. 2. In 203, if the received medical image is a breast ultrasound image, skin, subcutaneous fat, glandular tissue, retromammary fat, a pectoralis muscle, and a rib are detected as anatomical elements. In 205, the anatomical elements are analyzed based on anatomical context information including domain knowledge associated with relationships between the anatomical elements, probability information, and adjacent image information.

In 207, among anatomical element information of all of the analyzed anatomical elements, only a confidence level of one or more anatomical elements selected by a user is combined with the original image. For example, if skin, subcutaneous fat, glandular tissue, retromammary fat, a pectoralis muscle, and a rib are detected as anatomical elements, the user may select any desired anatomical element. For example, the user may select only skin, may select both subcutaneous fat and glandular tissue, or may select all of the detected anatomical elements. Then, anatomical element confidence level information of each of the selected anatomical elements is visually overlaid onto the original image. For example, any one or more of half-transparent layers of different colors distinguishing each of the selected anatomical elements, contours delineating each of the selected anatomical elements, text representing the names of each of the selected anatomical elements in the corresponding areas, and confidence levels of each of the selected anatomical elements may be visually overlaid onto the original image.

An apparatus for visualizing anatomical elements in a medical image may be implemented by a computing device that includes a processor, a memory, a user input device, and a presentation device. The memory is a medium that stores computer-readable software, applications, program modules, routines, or instructions each capable of performing a specific task when the computer-readable software, applications, program modules, routines, or instructions are executed by a processor.

The processor may read and execute computer-readable software, applications, program modules, routines, or instructions that are stored in the memory. The user input device may be a device enabling a user to input a command for a specific task to a processor or input data needed to perform a specific task. The user input device may include a physical or virtual keyboard, a keypad, a mouse, a joystick, a track ball, a touch-sensitive input device, or a microphone. The presentation device may include a display, a printer, a speaker, or a vibration device.

A computing device may be any of various devices, such as a smart phone, a tablet, a laptop, a desktop, a server, and a client device. The computing device may be a single stand-alone device, or a plurality of computing devices that interoperate with each other in a distributed environment.

A method of visualizing anatomical elements in a medical image may be implemented by a computing device that includes a memory storing computer-readable software, applications, program modules, routines, or instructions encoded to implement the method.

The various apparatuses for visualizing anatomical elements in medical images described above with reference to FIGS. 1-15 are merely exemplary. It will be apparent to one of ordinary skill in the art that different apparatuses with various combinations of elements fall within the scope of the claims and their equivalents. Components of an apparatus for visualizing anatomical elements in a medical image may be implemented by hardware that performs the functions of the respective components. In addition, the components of an apparatus for visualizing anatomical elements in a medical image may be implemented by a combination of computer-readable software, applications, program modules, routines, or instructions for performing a specific task when executed by a processor of a computing device, firmware, and hardware.

In addition, the various methods described above with reference to FIGS. 16 to 20 are merely exemplary. It will be apparent to one of ordinary skill in the art that different methods with various combinations of operations fall within the scope of the claims and their equivalents. Examples of a method for visualizing anatomical elements in a medical image may be coded by computer-readable software, applications, program modules, routines, or instructions that are able to perform a specific task when executed by a processor of a computing device. The computer-readable software, applications, program modules, routines, or instructions may be encoded in a programming language, such as Basic, Fortran, C, C++, or any other programming language known to one of ordinary skill in the art, and then compiled in a machine language.

The image receiver 31, the anatomical element detector 33, the analyzer 35, the anatomical context information 37, and the image combiner 39 in FIGS. 2 and 3, the lesion verifier 38, the image combiner 39, the domain knowledge 372, the probability information 374, and the adjacent image information 376 in FIG. 3, the feature map extractor 41, the feature map allocator 43, and the image labeler 45 in FIG. 4, and the skin detector 61, the subcutaneous fat detector 63, the glandular tissue detector 65, and the pectoralis muscle detector 67 in FIG. 6 that perform the operations described with respect to FIGS. 1-20 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for visualizing anatomical elements in a medical image, the apparatus comprising:
   a memory configured to store instructions therein; and
   at least one processor, upon execution of the instructions, configured to:
      receive a medical image,
      detect a plurality of anatomical elements from the medical image,
      verify a location of each of the plurality of anatomical elements based on anatomical context information comprising location relationships between the plurality of anatomical elements, and adjust the location of at least one of the plurality of anatomical elements based on a result of the verification,
      combine at least one piece of information related to the plurality of verified anatomical elements and the adjusted at least one anatomical element with the medical image, and
      display the medical image combined with the at least one piece of information,
   wherein the at least one piece of information to be combined with the medical image comprises confidence level information indicating a confidence level that each of the plurality of anatomical elements is actually an anatomical element,
   wherein the at least one information to be combined with the medical image is selected by a user from the information related to the plurality of verified anatomical elements and the adjusted at least one anatomical element, wherein the medical image is one of a plurality of continuous frames or one of a plurality of three-dimensional (3D) images, wherein the anatomical context information further comprises location information of anatomical elements detected from an adjacent frame of the medical image or an adjacent cross-section of the medical image, wherein the at least one processor is further configured to:
verify the location of each of the plurality of anatomical elements detected from the medical image based on the location information of the anatomical elements detected from the adjacent frame or the adjacent cross-section, wherein the medical image comprises a breast ultrasound image of a human breast captured using ultrasonic waves, wherein the at least one processor is further configured to detect, from the breast ultrasound image, any two or more of skin, fat, glandular tissue, muscle, or bone, and wherein the anatomical context information comprises location relationships between the any two or more of skin, fat, glandular tissue, muscle, or bone.

2. The apparatus of claim 1,
wherein the at least one processor is further configured to perform the verification and the adjustment based on the anatomical context information comprising the location relationships between the any two or more of skin, fat, glandular tissue, muscle, and bone.

3. The apparatus of claim 1, wherein the at least one processor is further configured to individually detect a respective one of the plurality of anatomical elements from the medical image.

4. The apparatus of claim 3, wherein the at least one processor is further configured to detect the respective one of the plurality of anatomical elements using any one of a deep learning technique, a sliding window technique, or a superpixel technique.

5. The apparatus of claim 1, wherein the at least one processor is further configured to detect the plurality of anatomical elements from the medical image simultaneously.

6. The apparatus of claim 5, wherein the at least one processor is further configured to detect the plurality of anatomical elements from the medical image simultaneously using any one of a deep learning technique, a sliding window technique, or a superpixel technique.

7. The apparatus of claim 5, wherein the at least one processor is further configured to detect the plurality of anatomical elements from the medical image simultaneously by extracting a plurality of feature maps from the medical image, allocating the plurality of feature maps to corresponding respective anatomical elements, and labeling a location in the medical image of a feature map allocated to the specific anatomical element as the specific anatomical element.

8. The apparatus of claim 1, wherein the at least one processor is further configured to adjust a detection result of the plurality of anatomical elements detected from the medical image using a conditional random field technique or a Markov random field technique.

9. The apparatus of claim 1,
wherein the anatomical context information further comprises information on a probability distribution of a location at which each of the plurality of anatomical elements is located in the medical image, and wherein the probability distribution is acquired from pre-established learning data.

10. The apparatus of claim 1, wherein the at least one piece of information related to the plurality of anatomical elements to be combined with the medical image comprises area information indicating an area of each of the plurality of anatomical elements in the medical image.

11. The apparatus of claim 10, wherein the area information comprises any one or any combination of a contour of an area of each of the plurality of anatomical elements, text representing a name of each of the plurality of anatomical elements, or a color distinguishing an area of each of the plurality of anatomical elements.

12. The apparatus of claim 10, wherein the confidence level information comprises any one or any combination of text displayed within an area of each of the plurality of anatomical elements, a color of a contour of an area of each of the plurality of anatomical elements, or a transparency of a contour of an area of each of the plurality of anatomical elements.

13. The apparatus of claim 1, wherein the at least one piece of information related to the plurality of anatomical elements to be combined with the medical image comprises any one or any combination of the following:

area information about an area of each of the plurality of anatomical elements in the medical image, a color or a transparency of a contour of an area of each of the plurality of anatomical elements, a color or a transparency of text representing a name of each of the plurality of anatomical elements, or a transparency of a color layer distinguishing an area of each of the plurality of anatomical elements.

14. The apparatus of claim 1, wherein the at least one processor is further configured to verify whether a region of interest (ROI) detected from the medical image is a lesion based on a lesion detection probability of an anatomical element in which the ROI is located.

15. A method of visualizing anatomical elements in a medical image, the method comprising:

receiving a medical image;

detecting a plurality of anatomical elements from the medical image;

verifying a location of each of the plurality of anatomical elements based on anatomical context information comprising location relationships between the plurality of anatomical elements;

adjusting the location of at least one of the plurality of anatomical elements based on a result of the verification;

combining at least one piece of information related to the plurality of verified anatomical elements and the adjusted at least one anatomical element with the medical image; and displaying the medical image combined with the at least one piece of information, wherein the at least one piece of information to be combined with the medical image comprises confidence level information indicating a confidence level that each of the plurality of anatomical elements is actually an anatomical element, wherein the at least one information to be combined with the medical image is selected by a user from the information related to the plurality of verified anatomical elements and the adjusted at least one anatomical element, wherein the medical image is one of a plurality of continuous frames or one of a plurality of three-dimensional (3D) images, wherein the anatomical context information further comprises location information of anatomical elements detected from an adjacent frame of the medical image or an adjacent cross-section of the medical image, wherein the verifying of the location of each of the plurality of anatomical elements comprises:

verifying the location of each of the plurality of anatomical elements detected from the medical image based on the location information of the anatomical elements detected from the adjacent frame or the adjacent cross-section, wherein the medical image comprises a breast ultrasound image of a human breast captured using ultrasonic waves, wherein the detecting of the plurality of anatomical elements comprises detecting, from the breast ultrasound image, any two or more of skin, fat, glandular tissue, muscle, or bone, and wherein the anatomical context information comprises location relationships between the any two or more of skin, fat, glandular tissue, muscle, and bone.

16. The method of claim 15, wherein the verifying and the adjusting comprise performing the verifying and the adjusting based on the anatomical context information comprising the location relationships between the any two or more of skin, fat, glandular tissue, muscle, or bone.

17. The method of claim 15, wherein the detecting of the plurality of anatomical elements comprises individually detecting respective ones of the plurality of anatomical elements from the medical image.

18. The method of claim 17, wherein the individually detecting of the respective ones of the plurality of anatomical elements comprises individually detecting the respective ones of the plurality of anatomical elements from the medical image using any one of a deep learning technique, a sliding window technique, or a superpixel technique.

19. The method of claim 15, wherein the detecting of the plurality of anatomical elements comprises simultaneously detecting the plurality of anatomical elements from the medical image.

20. The method of claim 19, wherein the simultaneously detecting of the plurality of anatomical elements comprises simultaneously detecting the plurality of anatomical elements using any one of a deep learning technique, a sliding window technique, or a superpixel technique.

21. The method of claim 19, wherein the simultaneously detecting of the plurality of anatomical elements comprises:

extracting a plurality of feature maps from the medical image, allocating the plurality of feature maps to corresponding respective anatomical elements, and labeling a location in the medical image of a feature map allocated to the specific anatomical element as the specific anatomical element.

22. The method of claim 15, wherein the adjusting comprises adjusting a detection result of the plurality of anatomical elements detected from the medical image using a conditional random field technique or a Markov random field technique.

23. The method of claim 15, wherein the anatomical context information comprises information on a probability distribution of a location at which each of the plurality of anatomical elements is located in the medical image, and wherein the probability distribution is acquired from pre-established learning data.

24. The method of claim 15, wherein the at least one piece of information related to the plurality of anatomical elements to be combined with the medical image comprises area information indicating an area of each of the plurality of anatomical elements in the medical image.

25. The method of claim 24, wherein the area information comprises any one or any combination of a contour of an area of each of the plurality of anatomical elements, text representing a name of each of the plurality of anatomical elements, or a color of an area distinguishing each of the plurality of anatomical elements.

26. The method of claim 15, wherein the confidence level information comprises any one or any combination of text within an area of each of the plurality of anatomical elements, a color of a contour of an area of each of the plurality of anatomical elements, or a transparency of a contour of an area of each of the plurality of anatomical elements.

27. The method of claim 15, wherein the at least one piece of information related to the plurality of anatomical elements to be combined with the medical image comprises any one or any combination of the following:

area information about an area of each of the plurality of anatomical elements in the medical image, a color or a transparency of an area of each of the plurality of anatomical elements, a color or a transparency of text representing a name of each of the plurality of anatomical elements, or a transparency of a color layer distinguishing an area of each of the plurality of anatomical elements.

28. The method of claim 15, further comprising verifying whether a region of interest (ROI) detected from the medical image is a lesion based on a lesion detection probability of an anatomical element in which the detected ROI is located.

29. A method of visualizing anatomical elements in a medical image, the method comprising:

detecting a plurality of anatomical elements from a medical image;

correcting a boundary of at least one of the plurality of anatomical elements to match an actual boundary of at least one of the plurality of anatomical elements in the medical image based on anatomical context information comprising location relationships between the plurality of anatomical elements;

combining at least one piece of anatomical element information of the at least one anatomical element having the corrected boundary with the medical image; and displaying the medical image combined with the at least one piece of anatomical element information, wherein the at least one piece of anatomical element information to be combined with the medical image comprises confidence level information indicating a confidence level that each of the plurality of anatomical elements is actually an anatomical element, wherein the at least one piece of anatomical element information to be combined with the medical image is selected by a user from anatomical element information related to the plurality of anatomical elements, wherein the medical image is one of a plurality of continuous frames or one of a plurality of three-dimensional (3D) images, wherein the anatomical context information further comprises location information of anatomical elements detected from an adjacent frame of the medical image or an adjacent cross-section of the medical image, wherein the correcting of the boundary of the at least one of the plurality of anatomical elements comprises:

correcting the boundary of the at least one of the plurality of anatomical elements detected from the medical image based on the location information of the anatomical elements detected from the adjacent frame or the adjacent cross-section, wherein the medical image comprises a breast ultrasound image of a human breast captured using ultrasonic waves, wherein the detecting of the plurality of anatomical elements comprises detecting, from the breast ultrasound image, any two or more of skin, fat, glandular tissue, muscle, or bone, and wherein the anatomical context information comprises location relationships between the any two or more of skin, fat, glandular tissue, muscle, and bone.

30. The method of claim 29, further comprising ignoring any detected anatomical element that does not correspond to an actual anatomical element in the medical image based on the anatomical context information.

\* \* \* \* \*